United States Patent [19]

Hagen et al.

[11] Patent Number: 5,138,098
[45] Date of Patent: Aug. 11, 1992

[54] 2-ACYL-6-METHYLNAPHTHALENE PREPARATION

[75] Inventors: Gary P. Hagen, West Chicago; Gregory E. Schmidt, Batavia; John M. Weis; Thomas G. Smith, both of Naperville, all of Ill.

[73] Assignee: Amoco Corporation, Chicago, Ill.

[21] Appl. No.: 669,377

[22] Filed: Mar. 14, 1991

[51] Int. Cl.$^5$ .................. C07C 45/45; C07C 45/80
[52] U.S. Cl. .................. 568/323; 568/319; 568/324
[58] Field of Search .................. 568/323, 319, 324

[56] References Cited

U.S. PATENT DOCUMENTS

| 4,593,125 | 6/1986 | Davenport et al. | 568/323 |
| 4,868,338 | 9/1989 | Magni et al. | 568/319 |

FOREIGN PATENT DOCUMENTS

| 3530145 | 2/1987 | Fed. Rep. of Germany | 568/323 |
| 3701960 | 8/1988 | Fed. Rep. of Germany | 568/323 |
| 54-135766 | 10/1979 | Japan | 568/323 |
| 267538 | 11/1986 | Japan | 568/323 |
| 61-05837 | 4/1987 | Japan | 568/324 |

OTHER PUBLICATIONS

Maki et al., Chem. Abst., vol. 107, #154,0882 (1987).

Primary Examiner—James H. Reamer
Attorney, Agent, or Firm—Thomas E. Nemo; William H. Magidson; Frank J. Sroka

[57] ABSTRACT

A regioselective acylation process is provided for coverting a 2-methylnaphthalene compound to a 2-acetyl-6-methylnaphthalene compound. The process is conducted under liquid phase conditions in an acylation inert solvent using a complexing agent which is regiospecific for the beta position of naphthalene and which is a thermally stable nitrohydrocarbon compound. Preferred such agents are nitrobenzene, o-nitrotoluene, and mesitylene. Also provided is a novel method for producing a 2-acetyl-6-methylnaphthalene compound of relatively high purity from isomer mixtures by recrystallization from a hydrocarbon solvent, such as n-octane, isooctane, or n-nonane.

30 Claims, 2 Drawing Sheets

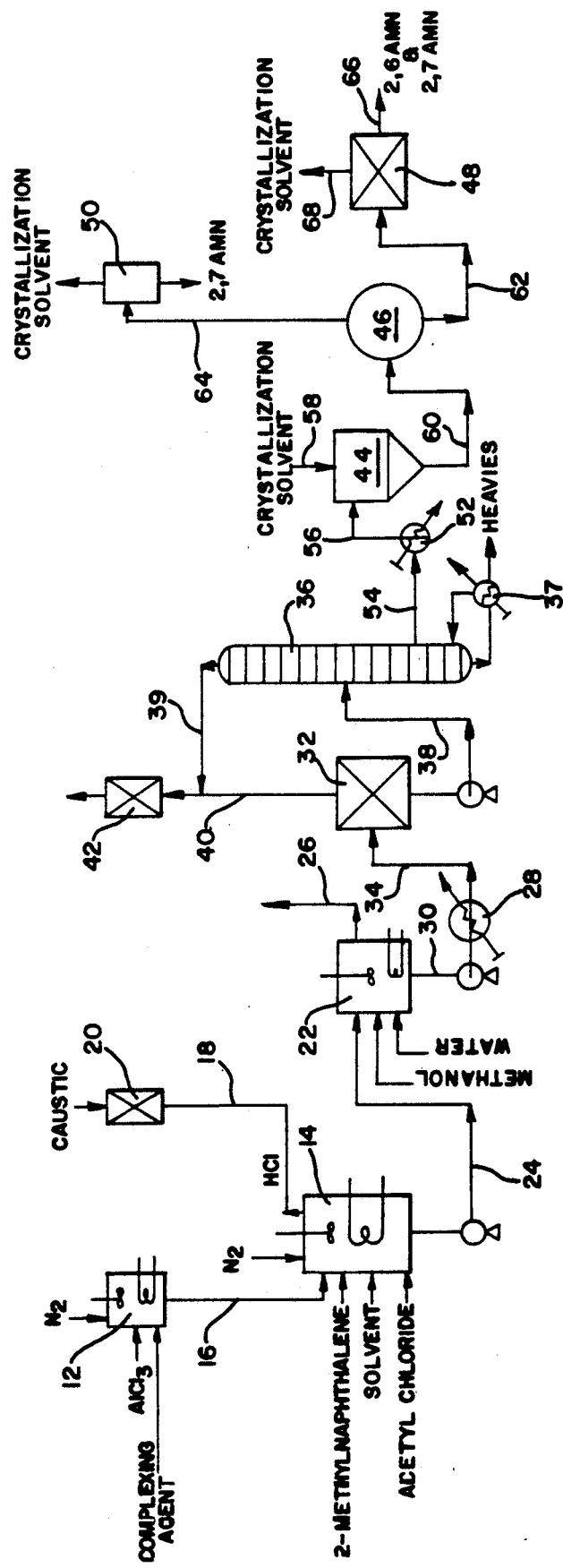

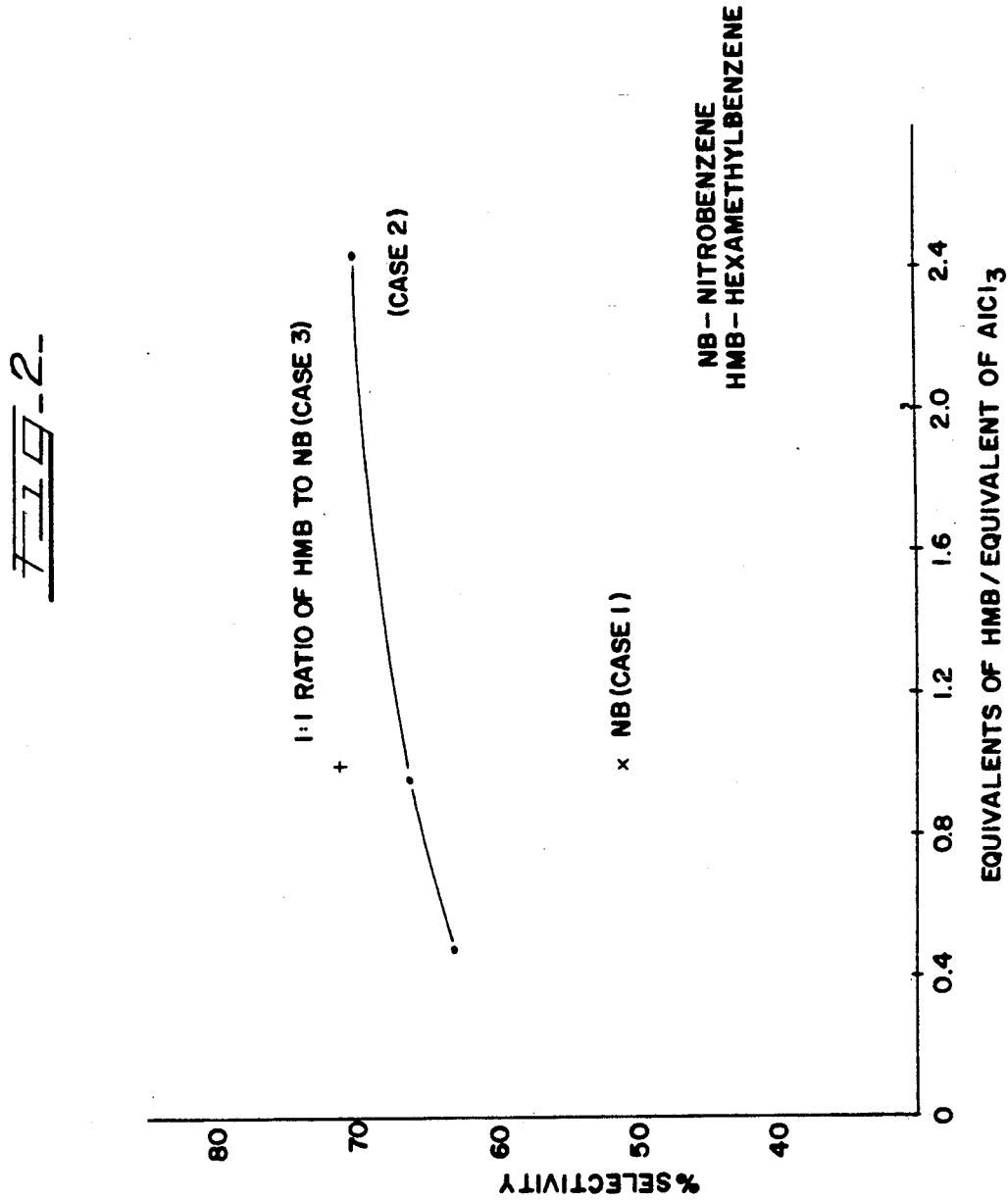

2-ACYL-6-METHYLNAPHTHALENE PREPARATION

FIELD OF THE INVENTION

This invention relates to regioselective acylation of 2-methylnaphthalenes to 2-acyl-6-methylnaphthalenes.

BACKGROUND OF THE INVENTION

2-Acetyl-6-methylnaphthalene (2,6-AMN) and 2-acetyl-6,7-dimethylnaphthalene (2,6,7-ADMN) are useful feedstocks for the production of 2,6-naphthalene dicarboxylic acid and 2,3,6-naphthalene tricarboxylic acid, respectively, by oxidation. Such acids are useful monomers for polymerization into high performance resins (or so-called engineering resins).

2,6-AMN and 2,6,7-ADMN can be prepared by various synthetic routes. One promising route involves Friedel-Crafts acylation of the corresponding 2-methylnaphthalene (2-MN) and 2,3-dimethylnaphthalene (2,3-DMN). The same tri-acid can be obtained by oxidation of 2-acetyl-3,7-dimethylnaphthalene, obtained by acylation of 2,6-dimethylnaphthalene (2,6-DMN), but the oxidation is believed to be undesirably sluggish.

Preparation of acyl aromatic ketones using Lewis acid metallohalide catalysts has been research subject matter since the original discoveries of Friedel and Crafts reported in 1877. The use of a single solvent and complexing agent such as nitrobenzene to promote beta position substitution in Friedel-Crafts acylations of naphthalene ring systems has been known for many years. A synthesis of 2,6-AMN by condensing acetyl chloride with 2-MN in nitrobenzene is believed to have been first reported by Kon and Weller, J. Chem. Soc., 1939:792. The reaction is illustrated by the following equation:

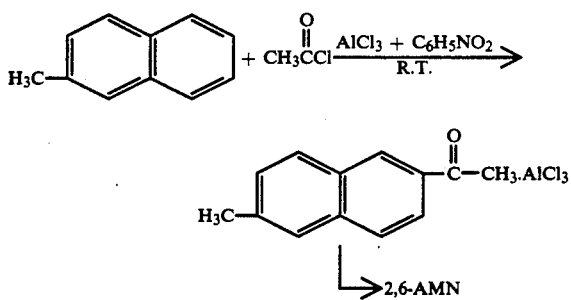

However, the reported isolated yield of 2,6-AMN was only 33 percent of theoretical. Since a 70 weight percent yield of the mixed isomeric ketones was isolated from the crude reaction mixture (by vacuum distillation), regiospecificity to the 2,6 isomer was characteristically undesirably low, probably on the order of about 50 percent.

A further disadvantage of this synthesis is that it requires the use of relatively large amounts of nitrobenzene which is undesirable particularly from a commercial processing standpoint because of the great toxicity of nitrobenzene. This material is categorized as a hazardous waste substance by the EPA. Thus, process waste water would have to be almost completely free of residual nitrobenzene to comply with EPA regulations.

An acylation procedure for 2-MN and for 2,3-DMN which would have high regiospecificity for producing beta position acylation and particularly the acetylation of the naphthalene nucleus, and which avoids the use of large amounts of nitrobenzene, would have value as a commercially practical procedure for making 2,6-AMN and 2,6,7-ADMN. The present invention provides such a procedure.

SUMMARY OF THE INVENTION

A regioselective process for making 2-acyl-6-methylnaphthalenes such as a 2-acetyl-6-methylnaphthalene is provided wherein a 2-methyl substituted naphthalene compound, such as 2-methylnaphthalene or 2,3-dimethylnaphthalene, is contacted in an acylation inert hydrocarbon solvent with an acylation complex constituted by a Friedel-Crafts catalyst, such as aluminum trichloride, a $C_2$–$C_5$ hydrocarbyl acylating agent such as acetyl chloride, and at least one thermally stable nitrohydrocarbon complexing agent which is regiospecific for the beta position of naphthalene. Nitrobenzenoid complexing agents are particularly preferred for this purpose.

The nitrohydrocarbon is present during the contacting in complexing agent quantities, but not in solvent quantities.

From the resulting reaction product mixture, wherein, for example, acetyl chloride was used as the acylating agent, the Friedel-Crafts catalyst, the solvent, and the unreacted methylnaphthalene starting material are removed to produce an acetylmethylnaphthalene isomer mixture rich in a 2-acetyl-6-methylnaphthalene compound. A highly purified 2-acetyl-6-methylnaphthalene compound is separatable from such isomer mixture by some convenient procedure, such as fractional distillation and/or crystallization.

The thermally stable nitrohydrocarbon complexing agent preferably is a nitrobenzenoid compound such as:
nitrobenzene;
an alkyl substituted nitrobenzene containing 1 through 4 carbon atoms per alkyl group;
a dinitrobenzene;
an alkyl substituted dinitrobenzene containing 1 through 4 carbon atoms per alkyl group;
a nitronaphthalene;
an alkyl substituted nitronaphthalene containing 1 through 4 carbon atoms per alkyl group;
a dinitronaphthalene;
an alkyl substituted dinitronaphthalene containing 1 through 4 carbon atoms per alkyl group;
a nitrobiphenyl;
an alkyl substituted nitrobiphenyl containing 1 through 4 carbon atoms per alkyl group;
a dinitrobiphenyl;
an alkyl substituted dinitrobiphenyl containing 1 through 4 carbon atoms per alkyl group;
and mixtures thereof.

However, other nitrohydrocarbon compounds can be utilized as the complexing agents as long as the basicity of the nitrohydrocarbon is no greater than that of permethylated nitrobenzene. Illustrative such nitrohydrocarbons are the sterically hindered, nitrosubstituted aliphatic hydrocarbon compounds, such as the nitroalkenes, the nitro-substituted cycloolefinic compounds, and the like, the nitro-substituted heterocyclic ring compounds such as the nitro furans, the nitro thiophenes, the nitro pyrroles, and the like, as well as the nitro-substituted metallocenes.

The solvent is an acylation inert hydrocarbon that is liquid at 0° C., is a solvent for organic reactants and organic reaction products, and is a member of the group consisting of aromatic hydrocarbons, halohydrocarbons, and mixtures thereof. The solvent is free from compounds containing nitro groups. Preferably, the solvent also dissolves the catalyst; however, this is not essential.

A principal feature of the present invention is the use of a thermally stable, preferably electronically hindered, nitrohydrocarbon, e.g., nitrobenzenoid, complexing agent which promotes regiospecific electrophilic substitution reactions on aromatic compounds, particularly the acylation and, more particularly, the acetylation of the beta position of naphthalene, when present in quantities sufficient to perform as complexing agent but insufficient to function as a solvent medium for the acylation reaction. Such use in combination with an acylation inert hydrocarbon solvent has never heretofore been known. Such use and combination avoids the toxicity and hazardous waste problems associated with prior art usage of nitrobenzene as the combined sole solvent and complexing agent in acylation reactions involving naphthalene.

Moreover, the relatively small amounts of nitrohydrocarbon complexing agents utilized in the practice of the invention dissolved in the solvent used as the reaction medium are surprisingly effective in producing regiospecificity for the beta position of naphthalene. Indeed, it has now been discovered that certain of such nitrohydrocarbon complexing agents are surprisingly superior in that they provide better selectively to for example 2,6-AMN than nitrobenzene on a mole for mole basis. Even a very low level of a nitrohydrocarbon compound, such as, for instance, a level as low as about 0.5 equivalents per equivalent of 2-MN in halohydrocarbon or benzene solvent, is highly effective in inducing regiospecific conversion of, for example, 2-MN to 2,6-AMN.

Another principal feature of the present invention is the surprising discovery that members of the preferred class of electronically hindered nitrobenzenoid compounds employed as complexing agents in the practice of this invention exhibit a synergistic effectiveness as regards regiospecificity for the beta position of naphthalene during acylation and particularly acetylation under aluminum trichloride catalyzed liquid phase conditions. Thus, such synergism is observed when such nitrobenzenoid complexing agents are employed in combination with members of another class of complexing agents whose members are likewise regiospecific for the beta position of naphthalene but which are carbon based and have at least one electronrich carbon center.

Members of such other class of complexing agents are typically selected from the group consisting of peralkylated aromatic hydrocarbons, including species from among peralkylated benzenes, peralkylated naphthalenes, and peralkylated biphenyl compounds; sterically hindered aliphatic compounds, including species from among alkenes, alkanes, and cycloolefinic hydrocarbons; peralkylated metallocenes, including species from among pentamethylcyclopentadienyl-group containing and hexamethylcyclohexadienyl-group containing metallocenes; peralkylated heterocyclic ring compounds, including species from among peralkylated furans, peralkylated thiophenes, peralkylated pyrroles, peralkylated pyridines, and peralkylated morpholines; and mixtures thereof. Presently preferred members of such other class of complexing agents comprise permethylated aromatic hydrocarbons, most preferably hexamethylbenzene; cycloolefinic hydrocarbons containing preferably two diene ring linkages per molecule, such as norbornadiene; and bis(pentamethylcyclopentadienyl metallocenes, such as pentamethylcyclopentadienyl ferrocenes.

For example, the particular combination of hexamethylbenzene and nitrobenzene in a halohydrocarbon solvent, such as methylene dichloride, exhibits a particularly large synergistic effect in providing high selectivity for forming 2,6-AMN from 2-MN. Generally, such a synergistic effect is achieved with relatively low total concentrations of such a combination of electron-rich carbon-based complexing agent with electronically hindered nitrobenzenoid complexing agents, such as total concentrations in the range of from about 0.5 to about 5 equivalents of the combined complexing agents per equivalent of 2-MN while using a ratio (expressed in terms of equivalents) of the electronically hindered nitrohydrocarbon complexing agent to electron-rich, carbon-based complexing agent in the range of about 10:1 to about 1:10.

Another feature of the present invention is the provision of preferred procedures for admixing the reaction components so as to maximize yields and selectivities for 2,6-AMN and 2,6,7-ADMN while utilizing a complexing agent of this invention.

Yet another feature of the present invention is the provision of a simple and convenient novel procedure for separating the Friedel-Crafts catalyst, such as aluminum trichloride, from the reaction product with a minimum of exotherm. The procedure involves the admixture with such product mixture of a monohydric alcohol containing 1 to 12 carbon atoms, inclusive, per molecule. A presently preferred such alcohol is a monoalkanol containing less than 5 carbon atoms per molecule. The most preferred alcohol for this purpose is methanol. Upon admixture, such an alcohol is believed to form a water soluble catalyst complex which is extracted with water from the reaction product mixture without decomposition of the catalyst into a gel. Preferably, at least two water extractions are used to extract the catalyst.

A still further feature of the present invention is the provision of a reliable novel procedure for recovering relatively high purity 2-acetyl-6-methylnaphthalene from a mixture of isomers of acetylmethylnaphthalene. The present recovery procedure involves the dissolution of an isomer mixture rich in a 2-acetyl-6-methylnaphthalene in an alkane solvent containing 5 to about 20 carbon atoms per molecule. n-Octane, isooctane, and n-nonane are the preferred solvents. Particularly preferred as the solvent is n-nonane. The starting isomer mixture used for the recovery procedure can be directly derived from the acetylation reaction (with intervening removal of $AlCl_3$, solvent, and residual 2-methylnaphthalene starting material), or can be a bottoms residue from a fractional distillation procedure during which relatively high purity 2-acetyl-6-methylnaphthalene has been already recovered from the acylation reaction products. After such a dissolution, the resulting solution is chilled, and then a crystallized 2-acetyl-6-methylnaphthalene is separated from the chilled solution.

Various other and further features, embodiments, and the like which are associated with the present invention will become apparent and better understood to those skilled in the art from the present description considered in conjunction with the accompanying drawings wherein presently preferred embodiments of the invention are illustrated by way of example. It is to be expressly understood, however, that the drawings and the associated accompanying portions of this specification are provided for purposes of illustration and description only, and are not intended as limitations on the invention.

BRIEF DESCRIPTION OF THE DRAWINGS

In the drawings:

FIG. 1 is a generalized flow diagram of a process embodying the present invention; and FIG. 2 is a plot illustrating the relationship between selectivity to 2-acetyl-6-methylnaphthalene (2,6-AMN) from 2-methylnaphthalene (2-MN) for various ratios of equivalents of hexamethylbenzene as complexing agent per equivalent of $AlCl_3$ with comparable selectivities being shown for nitrobenzene and a mixture of hexamethylbenzene with nitrobenzene.

DETAILED DESCRIPTION OF PREFERRED EMBODIMENTS

This acylation and, preferably, acetylation reaction of the present invention is carried out under liquid phase conditions in the presence of a Friedel-Crafts catalyst, such as aluminum trichloride, which is present in a finely divided, dispersed or dissolved form.

As above indicated, the thermally stable nitrohydrocarbon complexing agents of the present invention are regiospecific for the beta position of naphthalene. Preferably, they are electronically hindered. They are characterized by:

(1) inability to undergo irreversible acylation with an acyl chloride in the presence of Friedel-Crafts catalyst, and
(2) ability to bind with the Friedel-Crafts catalyst.

Thus, such a complexing agent functions, when present, for example, during catalytic acylation of a 2-methylnaphthalene compound to 2-acetyl-6-methylnaphthalene with acetyl chloride, to direct the production of a reaction product mixture containing an aromatic naphthalene ketone/Friedel-Crafts catalyst reaction product that is rich in 2-acetylmethylnaphthalenes. Suitable such thermally stable complexing agents can be drawn from among the various classes of the nitrohydrocarbon compounds above indicated.

As used herein, the term "2-methylnaphthalene compound" is generic to both 2-methylnaphthalene and 1,2-dimethylnaphthalene.

While acetyl chloride is the preferred acylating agent for acylating the 2-methyl substituted naphthalene compounds by the processes of this invention, other hydrocarbyl acylating agents, and preferably $C_2$–$C_5$ hydrocarbyl acylating agents, are suitable. Therefore, although most of the discussion presented in this application concerns the acetylation of the 2-methyl substituted naphthalenes using acetyl chloride as the preferred acylating agent, it is to be understood that other acylating agents, particularly the $C_2$–$C_5$ hydrocarbyl acylating agents, can be employed for acylating the 2-methyl substituted naphthalenes.

A $C_2$–$C_5$ hydrocarbyl acylating agent, as the term is herein used, means that the acylating agent delivers an acyl group having two to five carbon atoms to the 2-methyl substituted naphthalene compounds even though the agent itself may contain more carbon atoms. Illustrative $C_2$–$C_5$ hydrocarbyl acylating agents are the acyl halides having two to five carbon atoms and being either straight-chain, branched, saturated or unsaturated in structure. Preferably, the halide is chlorine or bromine. For example, acetyl bromide, propionyl bromide, propionyl chloride, and the like. Other $C_2$–$C_5$ hydrocarbyl acylating agents include the anhydrides of carboxylic acids wherein the acid portion of the anhydride has two to five carbon atoms and wherein said acid portion is either branched, straightchain, saturated or unsaturated, as, for example, acetic anhydride, propionic anhydride and the like. Mixed anhydrides are also suitable. Generally, when an anhydride is used as an acylating agent, a greater quantity of Friedel-Crafts catalyst is required as compared to when an acyl halide is used as an acylating agent.

As used herein, the term "Friedel-Crafts catalyst" includes not only aluminum chloride, but also other highly active metallic halides, including, for example, $AlBr_3$, $FeCl_3$, $FeBr_3$, $SbCl_5$, $SbBr_3$, $TiCl_4$, $NbCl5$), $GaCl_3$, $ZrCl_4$, $SbF_5$, $BF_3$, $AsF_5$, and the like. The purity of the halide may exert a considerable influence on the yield of product; for example, trace amounts of ferric chloride with aluminum chloride can increase overall product yield, or exert an accelerating effect on the acylation reaction. Concentrated sulfuric acid and other mineral acids can be used with the acetyl chloride in a two phase system with ether. In general, any of the known Friedel-Crafts catalysts is believed to be useful in the regioselective process of this invention where a 2-methylnaphthalene compound is acetylated with acetyl chloride.

The term "thermally stable" as used herein in relation to a nitrohydrocarbon compound (or nitrohydrocarbon complexing agent or nitrobenzenoid compound) has reference to the fact that such a compound (or complexing agent) is stable and does not deteriorate, degrade, decompose, or the like at temperatures employed in the practice of the present invention, such as temperatures below about 70° C. (158° F.).

The term "nitrohydrocarbon," as used herein describing the general class of suitable complexing agents, means a hydrocarbon bearing a nitro group ($-NO_2$) as a substituent and having a basicity no greater than that of permethylated nitrobenzene.

The term "nitrobenzenoid" as used herein, particularly with respect to a complexing agent has reference to an aromatic compound which is ring substituted by either one or two nitro groups ($-NO_2$) per molecule. The aromatic compound contains (a) a benzene ring, (b) a naphthalene ring, or (c) a biphenyl ring.

The term "lower" as used herein in relation to "alkyl" or other group has reference to the fact that such group contains not more than four carbon atoms each.

Examples of the preferred nitrobenzenoid compounds include nitrobenzene (a presently most preferred complexing agent), o-, m-, and p-dinitrobenzenes (including mixtures thereof), o-, m-, and p-nitrotoluenes, (including mixtures thereof), nitromesitylene, 2-tert-butyl-3,5-dinitro-1-isopropyl-4-methylbenzene, 2-tert-butyl-1,3-dinitro-4,5,6-trimethylbenzene, 1,2-dimethyl-3,4-dinitrobenzene, 1,2-dimethyl-3,5-dinitrobenzene, 1,2-dimethyl-4,5-dinitrobenzene, 1,3-dimethyl-2,5-dinitrobenzene, 1,4-dimethyl-2,3-dinitrobenzene, 1,4-dimethyl-2,5-dinitrobenzene, 1,3-dimethyl-4,5-dinitrobenzene, 1,3-dimethyl-2,4-dinitrobenzene, 2,3-dimethyl-1,4-dinitrobenzene, 2,5-dimethyl-1,3-dinitrobenzene, 12,3-dimethyl-4,6-dinitrobenzene, 1,2-dimethyl-3-nitrobenzene, 1,2-dimethyl-4-nitrobenzene, 1,3-dimethyl-2-nitrobenzene, 1,3-dimethyl-5-nitrobenzene, 1,4-dimethyl-2-nitrobenzene, 2,4dimethyl-1-nitrobenzene, 1,2-dinitrobenzene, 1,3-dinitrobenzene, 1,4-dinitrobenzene, 1-ethyl-2-nitrobenzene, 1-ethyl-3-nitrobenzene, 1-ethyl-4-nitrobenzene, 4-isopropyl-1-methyl-2-nitrobenzene, 1-isopropyl-2-nitrobenzene, 1-isopropyl-4-nitrobenzene, 1-nitro-2,3,5-trimethylbenzene, 1-nitro-2,4,5-trimethylbenzene, 2-nitro-1,3,5-trimethylbenzene.

Examples of suitable nitro group substituted naphthalene compounds include 1,3-dinitronaphthalene, 1,5-dinitronaphthalene, 1,8-dinitronaphthalene, 2-nitro-1-methylnaphthalene, 3-nitro-1-methylnaphthalene, 4-nitro-1-methylnaphthalene, 5-nitro-1-methylnaphthalene, 6-nitro-1-methylnaphthalene, 7-nitro-1-methylnaphthalene, 8-nitro-2-methylnaphthalene, 2-methyl-3-nitronaphthalene, 6-nitro-2-methylnaphthalene, 1-nitro-6-methylnaphthalene, 1-nitronaphthalene, 2-nitronaphthalene, and the like.

Examples of suitable nitro group substituted biphenyl compounds include 2,2'-dinitrobiphenyl, 2,4'-dinitrobiphenyl, 3,3'-dinitrobiphenyl, 4,4'-dinitrobiphenyl, 2-nitrobiphenyl, 3-nitrobiphenyl, 4-nitrobiphenyl, and the like.

Examples of suitable nitro groups substituted cycloolefins include nitrobicyclo [2.2.1] dienes, such as nitrobicyclo [2.2.1] heptadiene; nitrocyclopentadiene; and the like.

Examples of suitable nitro group substituted metallocene compounds include nitrocyclopentadienyl-group containing metallocenes, such as bis(nitrocyclopentadienyl) ferrocene, and also bis(nitrocyclopentadienyl cobaltocene); nitrocyclohexadienyl-group containing metallocenes, such as bis(nitrocyclohexadienyl) ferrocene, and also bis(nitrocyclohexadienyl) cobaltocene; and the like.

The acetylation process of the present invention is carried out under liquid phase conditions. The reactants and the complexing agent(s) are contacted in an acylation inert organic solvent that is a liquid at 0° C. (32° F.) and that is free from nitro substituents. The solvent solubilizes all reactants and the complexing agent(s). Also, the solvent exhibits substantially complete chemical inertness towards the reactants and the preferred, characteristically strongly acidic aluminum trichloride catalyst. The solvent also preferably dissolves the catalyst, but it is not necessary to impose this condition on a solvent because the acylation reaction will also proceed as a two-phase system wherein the catalyst, or a portion thereof, is in the form of a dispersed particulate solid or liquid in the liquid reaction solvent medium.

Presently preferred such solvents are selected from the group consisting of aromatic hydrocarbons, halohydrocarbons, and mixtures thereof.

Examples of suitable aromatic hydrocarbon solvents include benzene (presently preferred), lower alkyl substituted benzenes wherein each of the lower alkyl groups contains 1 to 4 carbon atoms, inclusive, and the like.

Examples of suitable halohydrocarbon solvents include methylene dichloride (presently preferred), 1,2-dichloroethane, and the like.

While mixtures of such solvents may be employed, if desired, solvent mixtures are not preferred since product separation on purification is simplified if only a single solvent is employed during an acetylation.

Each of the starting reactants (a 2-methylnaphthalene compound, and acetyl chloride) can be conventionally prepared or obtained commercially. It is presently preferred that each of such reactants, and also each of the other components including complexing agent and catalyst present in the reaction zone, have a purity of at least about 95 weight percent, and more preferably, a purity of at least about 99 weight percent.

The aluminum chloride, the acetyl chloride, and the complexing agent(s) are believed to form an acylation complex. To effect the desired acetylation, a catalytically effective amount of a Friedel-Crafts catalyst, such as aluminum trichloride, about 0.5 to about 5 equivalents of the complexing agent(s) per equivalent of the 2-methylnaphthalene compound, and about 0.5 to about 5 equivalents of the acetyl chloride per equivalent of such 2-methylnaphthalene compound are combined in an acylation inert solvent. In a preferred mode of practicing this invention, about 0.8 to about 1.2 equivalents of AlCl₃ per equivalent of the 2-methylnaphthalene compound, about 0.2 to about 2 equivalents of the complexing agent(s) per equivalent of the 2-methylnaphthalene compound, and about 0.8 to about 1.2 equivalents of the acetyl chloride per equivalent of the 2-methylnaphthalene compound are combined in the solvent.

As a present preference, the weight ratio of solvent to 2-methylnaphthalene compound is in the range of about 1:1 to about 20:1; however, higher and lower such ratios can be employed without departing from the spirit and scope of this invention.

While the acylation reaction of the present invention wherein a 2-methylnaphthalene compound is combined with the acylation complex is preferably carried out at substantially room (ambient) temperature conditions, one skilled in the art will appreciate that temperatures somewhat elevated or lowered relative to room temperature can be employed, if desired. For example, temperatures in the range of about 10° C. to about 40° C. (50° F. to 104° F.) are suitable, although higher and lower temperatures can be employed without departing from the spirit and scope of the present invention. However, at elevated temperature, yields of desired 2-acetyl-6-methylnaphthalenes may be reduced relative to the corresponding yields achieved at room temperatures, owing particularly to side reactions.

A process flow diagram illustrating the overall process for regioselective acetylation of 2-methylnaphthalenes to 2-acetyl-6-methylnaphthalenes is shown in FIG. 1. Mixing tank 12, equipped with cooling coils, is provided upstream from reactor 14 and serves as a vessel for the preparation of the ambident complex constituted by the catalyst and the nitrohydrocarbon complexing agent. Mixing tank 12 communicates with reactor 14 by means of the complex feed line 16. Reactor 14 also communicates with catalyst quench tank 22 downstream via product line 24 and with caustic scrubber 20 via line 18.

Catalyst quench tank 22 receives an admixture of reaction product, reactants and catalyst complex through product line 24. An aqueous waste stream containing primarily a monohydric alcohol, such as methanol, the Friedel-Crafts catalyst, and water, is decanted from quench tank 22 through line 26 while an admixture of reaction products proceeds first to a heater means 28, such as a hot oil heater, via line 30 and then to flash distillation vessel 32 via line 34.

A bottom stream from flash distillation vessel 32, containing AMN isomers and some residual complexing agent, is fed via line 38 to vacuum distillation column 36 equipped with reboiler 37, while the flash distillation overhead product, chiefly constituted by the complexing agent and water and optionally the solvent, leaves the flash distillation vessel 32 via line 40 and passes through drier 42. Downstream from vacuum distillation column 36 are provided, in interconnected series, crystallizer 44, centrifuge 46 and drier 48.

A product cut, e.g., substantially the 2,6-AMN and the 2,7-AMN isomers, is withdrawn from column 36 through line 54 and passed to heat exchanger 52. Thereafter, the product cut is passed to crystallizer 44 via line 56. Solvent feed line 58 supplies a crystallization solvent to crystallizer 44. Product crystal-containing mother liquor from crystallizer 44 enters centrifuge 46 through line 60.

Crystalline product from centrifuge 46 is passed to drier 48 via line 62, and the recovered crystallization solvent is passed to liquid separator 50 via line 64. Dried product exits drier 48 via product line 66, and any crystallization solvent introduced into drier 48 along with the wet crystalline product via line 62 exits the drier 48 via line 68.

The present acetylation process can be practiced as a batch process as well as a continuous process. The exact manner in which the reactants, the catalyst, and the complexing agent(s) are brought together in solution in order to carry out the desired acetylation reaction appears to be relatively unimportant from the standpoint of achieving regiospecificity for the beta position of naphthalene using complexing agent(s) of this invention compared to results achieved under corresponding conditions without the use of a complexing agent of this invention. When a complexing agent of the present invention is present, the beta position selectivity achieved in this reaction is increased compared to the selectivity results obtained when the identical reaction is carried out in the absence of such complexing agent(s) but in a solvent as herein described.

When the nitrohydrocarbon complexing agent is present in quantities greater than about 5 equivalents per equivalent of the 2-methyl substituted naphthalene reactant, then it appears that such complexing agent is present in a quantity that is greater than is needed for achieving complexing agent activity, and the excess quantity of such agent then appears to behave as a solvent medium. Typically when nitrobenzene is used as the solvent and as the complexing agent, the quantity of nitrobenzene used is about 16 equivalents of nitrobenzene per equivalent of 2-MN. When nitrobenzene was used in the prior art in the conversion of 2-MN to 2,6-AMN, the nitrobenzene functioned both as a complexing agent and as a solvent. When, in accord with the present invention, the nitrobenzene is used in an amount suitable for achieving complexing agent activity (as above indicated), and a solvent of the type taught herein in effect replaces the remainder of the nitrobenzene that was used in the prior art as the solvent medium for such reaction, then surprisingly it is found that the regiospecificity of the nitrobenzene as regards the beta position of naphthalene remains high compared to the regiospecificity of nitrobenzene when it comprises both complexing agent and solvent.

Experiments were carried out to determine the effects on the 2,6-AMN synthesis of low levels of nitrobenzene as a complexing agent in various types and quantities of solvents, as shown in Table I below (and in the associated examples). Conducting the reaction in benzene solvent in the absence of a nitrohydrocarbon complexing agent provided only an 18 percent selectivity to 2,6-AMN at a solvent ratio of 16.6 ml benzene/gram of 2-MN. Replacement of a small portion of the benzene solvent with nitrobenzene (3.8 eq./eq. 2-MN) provided a significant improvement in selectivity to 58 percent. Although this value is not as high as the 72 percent obtained in pure nitrobenzene solvent, the result demonstrates that moderately but surprisingly high selectivities are obtainable with much lower usage of nitrobenzene (3.8 eq./gm of 2-MN compared to 23 eq./gm of 2-MN) for pure nitrobenzene solvent.

Significant selectivity enhancement is also observed when nitrobenzene is employed in small amounts in halocarbon solvents. For example, a single equivalent of nitrobenzene per equivalent of 2-MN dissolved in methylene dichloride solvent provided 51 percent selectivity to 2,6-AMN in comparison to only 9 percent obtained in pure methylene chloride. For another example, 2.5 eq. of nitrobenzene in 1,2-dichloroethane solvent provided 55 percent selectivity to 2,6-AMN in comparison to only 21 percent obtained in pure 1,2-dichoroethane.

Levels of nitrobenzene complexing agent as low as 1 equivalent per equivalent of 2-MN reactant in benzene, in methylene dichloride, or ethylene chloride provide selectivities to 2,6-AMN much enhanced over those obtained with these solvents in the absence of the complexing agent.

High solvent ratios of, for example, benzene or halohydrocarbon solvent (expressed conveniently in ml/gm 2-MN) do not necessarily favor improved selectivity to 2,6-AMN. For example, two of the best results with nitrobenzene complexing agent (3.8 eq./eq. 2-MN) were obtained at a low ratio of 5.5 ml of benzene or ethylene dichloride per gram of 2-MN (60 percent and 62 percent selectivity, respectively). This effect is in contrast to that observed when the 2,6-AMN synthesis is carried out in pure nitrobenzene solvent, in which case the selectivity decreases significantly with decreasing solvent ratio.

The discovery of the present invention that a nitrohydrocarbon, such as nitrobenzene, can be an effective regiospecific complexing agent for the beta position of naphthalene when employed in quantities that are grossly insufficient for solvent purposes but which are sufficient for complexing agent purposes not only enables one to use substantially less nitrobenzene without sacrificing appreciably the desired regiospecificity favoring 2,6-AMN formation from 2-MN, which is desirable for environmental reasons as above explained, but also permits enhancement of the ultimate product (i.e., 2,6-AMN) yield. The boiling point of nitrobenzene is high (210° C.) and recovery of nitrobenzene as a solvent must be carried out at reduced pressure in order to minimize polymerization of the 2,6-AMN product. Furthermore, the freezing point of nitrobenzene is high (5.7° C.), and reactions in accord with the present invention could not be carried out at the desired low temperatures which favor high selectivities to 2,6-AMN. Therefore, the ability to reduce substantially the amount of nitrobenzene needed to obtain the regiospecificity achieved at 100 percent use levels of single combined solvent and complexing agent as taught by the prior art has immediate significant and desirable consequences.

To show the effect of increasing steric hindrance on the nitrobenzenoid complexing agents for acylation of 2-methyl substituted naphthalene reactants in accord with this invention, nitrobenzene, o-nitrotoluene, and nitromesitylene were compared. Since nitromesitylene is a solid, the procedure used involved a preliminary dissolution of each nitrobenzenoid compound in 25 ml of ethylene dichloride for each test. The equivalent ratio in all three tests was 2.48 mol of the nitrobenzenoid compound per mole of 2-MN, and the solvent ratio was 13.8 ml of ethylene dichloride per gram of 2-MN. Conversion (measured after 24 hours) was similar for all three tests at about 83 to about 90 percent. Selectivity extended a full 9 percent from nitrobenzene, which was 54.9 percent, to o-nitrotoluene, which was 65.1 percent, and then fell slightly with nitromesitylene, which was 62.5 percent.

Nitrobenzene and o-nitrotoluene were also compared as neat (i.e., pure) solvents (16.6 ml/gm of 2-MN, 20–23 eq./eq. 2-MN) for the 2,6-AMN product synthesis. At high conversion (81–85 weight percent at 24 hours of reaction time based on 2-MN), the selectivity obtained with o-nitrotoluene was 75 percent compared to 71.5 percent with nitrobenzene.

These results clearly demonstrate that o-nitrotoluene and nitromesitylene are superior to nitrobenzene as complexing agents for promotion of regiospecificity to the 2,6-AMN product. Other nitrohydrocarbon compounds within the scope of this invention having steric and/or electron withdrawing properties are also believed to be useful complexing agents.

The nitro group containing organic compounds previously known to the prior art which directed aluminum trichloride acylation to the beta position of naphthalene ring systems involve isoelectronic groups and are known to form loose sigma complexes with $AlCl_3$.

In the practice of the present invention, it has been discovered that certain component admixing or addition procedures for bringing the components together at the time of the acetylation reaction can also result in higher conversions and higher selectivities than do other addition procedures.

For example, the following addition procedures were evaluated under similar reaction conditions:
(a) addition of acetyl chloride to a solution of 2-MN, $AlCl_3$ and complexing agent (herein termed the Bouveault method);
(b) addition of 2-MN to a solution of acetyl chloride, $AlCl_3$ and complexing agent (herein termed the Perrier method);
(c) addition of $AlCl_3$ to a solution of 2-MN acetyl chloride and complexing agent (herein termed the Elbs method);
(d) addition of acetyl chloride to a solution of $AlCl_3$ followed by addition of the resulting solution to a solution of 2-MN and complexing agent (herein termed the retro-Perrier or solvated complex addition method);

In the retro-Perrier addition procedure, either the complexing agent can be dissolved with the Friedel-Crafts catalyst, such as aluminum trichloride, and the acetyl chloride, or the complexing agent can be dissolved with the 2-MN. In general, the location of the complexing agent need not be defined by the addition method; it is only required that the complexing agent be compounded with acetyl chloride, a Friedel-Crafts catalyst, such as aluminum trichloride, and the 2-methylnaphthalene compound.

From the standpoint of achieving high conversion and high selectivity, when acetylating 2-methylnaphthalene to produce 2-acetyl-6-methylnaphthalene, a presently preferred addition procedure involves the above indicated retro-Perrier procedure in which a preformed solution of acetyl chloride and aluminum trichloride most preferably in methylene dichloride is added to a separately preformed solution of 2-MN and complexing agent in the same solvent. In such addition procedure, methylene dichloride is the solvent for both such starting solutions, and the nitrohydrocarbon complexing agent is preferably a nitrobenzenoid compound, more preferably nitrobenzene or nitrotoluene.

Method (a) the Bouveault method, provided a 75 percent conversion to 2,6-AMN based on 2-MN with a 71 percent selectivity to 2,6-AMN using nitrobenzene complexing agent.

Method (b), the Perrier method, provided a 78 percent conversion to 2,6-AMN based on 2-MN with a 70 percent selectivity to 2,6-AMN using nitrobenzene complexing agent.

Method (c), the Elbs method, provided an 83 percent conversion to 2,6-AMN based on 2-MN with an 81 percent selectivity to 2,6-AMN using nitrobenzene complexing agent. Method (c) thus provided an 11 percent improvement in selectivity over method (b).

The foregoing addition procedures are also suitable for producing 2,6,7-ADMN from 2,3DMN.

The presently most preferred nitrobenzenoid complexing agents for use in the practice of this invention are o-nitrotoluene and nitromesitylene. When, as the examples hereinbelow illustrate, such preferred materials were each evaluated in various solvents as regards capacity for beta directing during the acetylation of 2-MN with acetyl chloride and aluminum trichloride catalyst, excellent and unexpected high selectivity was characteristically achieved.

Unexpectedly, it was discovered that acetylation with thermally stable nitrohydrocarbon complexing agents of this invention can be synergistically enhanced by using such complexing agents in combination with electron-rich, carbon-based complexing agents which are also regiospecific for the beta position of naphthalene. Members of such a class of electron-rich, carbon-based complexing agents have been characterized hereinabove, and preferred such complexing agents indicated.

The utilization of such electron-rich, carbon-based complexing agents in a regioselective Friedel-Crafts acetylation process for converting a 2-methyl substituted naphthalene reactant to a 2-acetyl-6-methyl substituted naphthalene is described in copending U.S. patent application Ser. No. 486,783, filed on even date herewith and entitled "Preparation of 2-Acetyl-6-Methylnaphthalenes", now U.S. Pat. No. 5,026,917.

The use of such a synergistic combination of at least one such nitrohydrocarbon compound with at least one such carbon-based, electron-rich complexing agent provides enhanced selectivities for producing 2-methyl-6-methylnaphthalene compounds from 2-methylnaphthalene compounds and acetyl chloride under liquid phase conditions with aluminum trichloride catalyst. Presently preferred are combinations of (a) nitrobenzene (most preferred), o-nitrotoluene, or nitromesitylene with (b) hexamethylbenzene.

When even low total combined levels of such nitrohydrocarbon complexing agents with such electron-rich, carbon-based complexing agents are employed as solutes in the acylation inert solvent, higher selectivities to 2-acetyl-6-methylnaphthalene products from a 2-methylnaphthalene reactant can be achieved than can be obtained by using a complexing agent from either of such respective classes of complexing agents alone at equivalent use rates.

Highest (presently most preferred) selectivity to 2,6-AMN from 2-MN is achieved by use of the aforeindicated retro-Perrier addition procedures in which a methylene dichloride solution of acetyl chloride and AlCl$_3$ is added to a solution containing 2-MN and a combination of nitrobenzene and hexamethylbenzene. Thus, a 71 percent selectivity to 2,6-AMN with a methylene dichloride solvent system containing 0.5 equivalent hexamethylbenzene per equivalent of 2-MN and 0.5 equivalent of nitrobenzene per equivalent of 2-MN. This result compares favorably with the 72 percent selectivity obtained at similar reaction conditions with pure nitrobenzene solvent using 15.6 equivalents of nitrobenzene per equivalent of 2-MN and a solvent ratio of 11.3 ml nitrobenzene per gram of 2-MN. The conversion of 2-MN using such combination was high, being in the range of about 82 to about 91 percent based on 2-MN.

Referring to the appended FIG. 2 and Table IV, below, together with the supporting Examples 29 through 33, the effectiveness of the presently most preferred combination of nitrobenzene and hexamethylbenzene is illustrated. When, for example, nitrobenzene and hexamethylbenzene are individually employed as complexing agents in equimolar quantities in a solvent such as methyl dichloride (presently most preferred), significant differences result. Thus, replacement of one equivalent of nitrobenzene per equivalent of 2-MN in methylene dichloride by an equivalent of hexamethylbenzene per equivalent of 2-MN in methylene dichloride resulted in a 15 percent increase in selectivity to 2,6-AMN, specifically, from 51 percent to 66 percent selectivity, and a 14 percent decrease in selectivity to 2,8-AMN, the major by-product produced. When a combination of 0.5 equivalents per equivalent of 2-MN of each of nitrobenzene and hexamethylbenzene was employed, there resulted a further 5 percent selectivity increase, specifically, to 71 percent selectivity, and a 5 percent decrease in selectivity to 2,1-AMN, a secondary by-product.

Referring to FIG. 2, the effect of hexamethylbenzene concentration on selectivity of 2-MN to 2,6-AMN was plotted using methylene dichloride solvent at a solvent ratio of 16.6 ml methylene dichloride per gram of 2-MN, a reaction time of one hour, a reaction temperature of 0° C. (32° F.), and an AlCl$_3$ equivalent ratio to 2-MN of 1.0 all while employing:

Case 1: a ratio of 1 equivalent of nitrobenzene per equivalent of AlCl$_3$;

Case 2: various ratios of hexamethylbenzene equivalents per equivalent of AlCl$_3$; and Case 3: a ratio of 1 equivalent of a combination of nitrobenzene and hexamethylbenzene per equivalent of AlCl$_3$ (using 0.5 equivalent of each of nitrobenzene and hexamethylbenzene per equivalent of AlCl$_3$).

The various respective ratios of hexamethylbenzene equivalents per equivalent of AlCl$_3$ employed were 0.48 0.897 and 2.42, as shown in the group of FIG. 2. The addition procedure method was that hereinabove termed the retro-Perrier procedure and involved addition of a solution of complexing agent, aluminum chloride and acetylchloride to a solution of 2-MN. The results indicate that:

(1) even though for identical equivalent ratios of each of nitrobenzene and hexamethylbenzene to AlCl$_3$ used separately, hexamethylbenzene provides about a 29.1 percent greater selectivity than achieved with nitrobenzene;

(2) nevertheless, for identical equivalent ratios of each of:

(a) a combination of nitrobenzene and hexamethylbenzene;

(b) nitrobenzene only; and (c) hexamethylbenzene only, such a combination (a) provides about a 7.4 percent greater selectivity than hexamethylbenzene alone and about a 38.7 percent greater selectivity than nitrobenzene alone.

Such results clearly demonstrate that the combination of nitrohydrocarbon complexing agent(s) and electron-rich, carbon-based complexing agent(s) results in a greater selectivity to 2-acetyl-6-methylnaphthalenes from 2-methylnaphthalene reactant than the selectivity achievable by using each of such agents separately. Thus, and for example, such results show that the combination of nitrobenzene and hexamethylbenzene as regards selectivity to 2,6-AMN from 2-MN exerts a synergistic effect.

In general, when employing a combination of nitrohydrocarbon complexing agent(s) with electron-rich, carbon-based complexing agent(s), it is preferred to employ a total of about 0.5 to 5 equivalents of such a combination per equivalent of 2-methylnaphthalene reactant; however, larger and smaller total equivalent weights of such a combination can be employed in any particular practice situation without departing from the spirit and scope of the present invention. Also, in general, in such a combination, the equivalent ratio of nitrohydrocarbon compound(s) to electron-rich, carbon-based compound(s) is preferably in the range of about 10:1 to 1:10, and more preferably in the range of about 4:1 to 1:4; however, higher and lower such ratios can be employed in any particular practice situation without departing from the spirit and scope of the present invention. It is presently most preferred to employ, in any given such combination, an equivalent ratio of about 1:1 for the nitrobenzenoid compounds present to the electron-rich carbon-based compounds present.

In acetylation procedures utilizing nitrohydrocarbon complexing agents which are solids at ambient conditions, reaction temperatures sufficient to keep the nitrohydrocarbon complexing agent in solution are needed. When the solvent is benzene, ethylene dichloride, methylene dichloride or 1,2-dichloroethane, reaction temperatures in the range from ambient up to the reflux temperature of the solvent are utilized to keep the nitrobenzenoid complexing agent in solution. At the end of an acylation procedure, some of the nitrohydrocarbon compound can be separated by cooling the liquid reaction product mixture, thereby crystallizing the nitrohydrocarbon compound, and then separating the crystals. Suitable chilling temperatures fall in the range of about −78° C. to about 0° C. (−108.4° F. to 32° F.). Also, partial evaporation of the solvent can be used to induce such a crystallization. In a commercial embodiment of the present invention, such a crystallization procedure provides a convenient and presently preferred technique for separation and reuse of such a complexing agent, as desired.

After the acetylation reaction, product separation and recovery procedures are implemented.

It is presently preferred to remove first from the liquid reaction product mixture that is believed to contain an aromatic ketone/Friedel-Crafts catalyst reaction product, preferably a mixture which contains substantially all of the Friedel-Crafts catalyst, such as aluminum trichloride. If and when the catalyst is not fully dissolved, and so is present in the liquid reaction products at least in part as a separate phase, then the liquid reaction product can be conveniently separated therefrom by an appropriate phase separation expedient.

A presently more preferred procedure for separating the dissolved catalyst is to add to a liquid reaction product a water-extractable aliphatic monohydric alcohol containing up to about 12 carbon atoms per molecule, inclusive, as a solubilizing agent. Preferred such alcohols are monoalkanols containing 1 to 4 carbon atoms per molecule.

Examples of such alcohols include methanol ethanol, propanol, isopropanol, the butanols, and the like. Particularly preferred for this purpose is methanol.

The alcohol forms a complex with the catalyst which complex is subsequently readily extractable with water from the resulting liquid admixture without decomposition of the catalyst, i.e., AlCl$_3$, into a gel, or the like.

A presently preferred procedure involves adding with agitation about 1 to about 5 equivalents of the alcohol per equivalent of catalyst to such a liquid product reaction mixture. A two-phase admixture is produced in which the relatively lighter aqueous phase comprises extracted alcohol/catalyst complex in an aqueous solution, and the relative heavier phase is an organic liquid phase containing the product. Preferably, the quantity of water so added is at least sufficient to produce an aqueous phase which, after phase separation, is at least equal in volume to the volume of the organic liquid phase.

The aqueous phase is isolated and can be discarded. The remaining organic liquid phase can be extracted one or more additional times in a similar manner. The ultimately isolated resulting lower organic liquid phase comprises a solution of residual complexing agent, unreacted 2-methylnaphthalene compound, and the product 2-acetyl-6-methylnaphthalene isomer mixture.

Those skilled in the art will appreciate that, as an alternative to the above described preferred procedure of alcohol/catalyst complex formation followed by water extraction, one of the various Friedel-Crafts catalyst separation procedures known to the art may be used in order to isolate the product containing organic liquid phase. For example, either concentrated hydrochloric acid or concentrated ammonium hydroxide may be added to a liquid product mixture for achieving complex formation thereof with the aluminum trichloride. If the resulting exotherm is undesirable, it can be reduced by the slow addition of the reactants or by cooling.

For example, concentrated hydrochloric acid can be added to a reaction product admixture with crushed ice.

For another example, concentrated ammonium hydroxide can be admixed with a chilled reaction product mixture.

Thereafter, the resulting system, whether containing concentrated HCl or concentrated NH$_4$OH, is extracted with an organic solvent, such as methylethyl ether, diethyl ether, or the like.

After mixing or otherwise accomplishing an extractable catalyst complex, the catalyst containing layer is conventionally separated from the organic layer containing the desired product. The resulting desired organic layer can then be further washed with water, if desired. The resulting washed organic layer can be dried by conventional means, e.g., with magnesium sulfate, or the like, filtered, and subjected to evaporation so as to remove at least about one-half of the organic solvent liquid present. Evaporation can be carried out using a conventional rotary evaporator, or the like.

After the removal of the catalyst, the complexing agent(s), solvent, and residual 2-MN are separated and removed from the 2-acetyl-6-methylnaphthalene product isomer mixture. No special procedure need be used for separation of solvent, residual complexing agent, and residual 2-MN.

The obtained mixture of the various acetylmethylnaphthalene isomers is subjected to separation procedure(s) to recover therefrom a desired high purity 2-acetyl-6-methyl substituted naphthalene product. Any convenient isomer mixture separation technique can be employed, including a combination of flash distillation, fractional distillation, and crystallization; or the like.

When 2-methylnaphthalene is the starting material, the product isomer mixture is rich in 2-acetyl-6-methylnaphthalene. The principal additional isomers present are 2-acetyl-8-methylnaphthalene, 2-acetyl-1-methylnaphthalene, and 2-acetyl-7-methylnaphthalene.

When 2,3-dimethylnaphthalene is the starting material, the product isomer mixture is rich in 2-acetyl-6,7-dimethylnaphthalene. The principal other isomers present are not observed in sufficient quantity to analyze and are not now identified. It is theorized that, if present in identifiable amounts, such isomers would be 1-acetyl-2,3-dimethylnaphthalene and 5-acetyl-2,3-dimethylnaphthalene in trace amounts.

In, for example, the case of a flash distillation of an isomer mixture constituting a reaction mixture using nitrobenzene as the nitrohydrocarbon, such can be heated, for example, to about 260° C. (500° F.) at 200 psi and flashed down to 4 psia. The resulting bottoms stream contains AMN isomers and residual nitrobenzene. Approximately 30 percent of the total nitrobenzene remains in the bottoms stream. The obtained overhead stream contains nitrobenzene which is conveniently recycled to the acylation reactor after drying.

In the case of fractionation using such an isomer mixture, the mixture is conveniently subjected to a 2-pass procedure. The bottoms from a flash distillation such as above described can comprise the first pass stream while the second pass stream can comprise the bottoms from the first pass plus an inert high boiling diluent. The product from the first pass is an overhead stream comprised of nitrobenzene and 2-MN, while the bottoms stream therefrom comprises mixed isomers free of nitrobenzene and 2-MN. The product from the second pass comprises (a) an overhead stream comprised of all isomers except 2,6-AMN and 2,7-AMN, (b) a so-called heart cut stream of 87 weight percent 2,6-AMN and 13 weight percent 2,6-AMN on a 100 weight percent basis, and (c) a bottoms stream comprised of the inert high boiling diluent. Such a fractionation is conveniently practiced continuously using about 50 mm Hg pressure and about 288° C. (550° F.) reboiler temperature, about a 10:1 reflux ratio, and about a 20 to 30 tray distillation column. A low residence time in the reboiler is preferred.

In the case of crystallization of such an isomer mixture, the heart cut from the above indicated second pass distillation can be used as the feed stock. The product can typically comprise about 95 weight percent 2,6-AMN and 5 weight percent 2,7-AMN on a 100 weight percent basis. The crystallization is conveniently practiced by feeding in 2 parts by weight of n-nonane preheated to about 38° C. (100° F.) for admixture with such heart cut. The mixture crystallizes at 15.6° C. (60° F.), and the solid product is separated by centrifuge and dried. The n-nonane recovered is recycled.

In the case of each such isomer mixture, fractional distillation is a convenient procedure that can be employed to produce a product of a desired purity level. For reasons of subsequent processing, e.g., oxidation to the corresponding carboxylic acid, and of ultimate product utilization, a product purity of at least about 95 weight percent is presently preferred for each of the isolated 2,6-AMN and 2,6,7-ADMN.

A 95 weight percent pure 2,6-AMN product is characteristically comprised of at least about 95 weight percent 2,6-AMN with the remainder thereof being primarily the 2,7-AMN isomer, while a 95 weight percent pure 2,6,7-ADMN product is characteristically comprised of at least about 95 weight percent 2,6,7-ADMN with the remainder thereof being as above indicated.

In one aspect, the present invention provides a new and very useful method for obtaining 2,6-AMN of relatively high purity and in a relatively high yield. This method involves recrystallization using as a solvent an alkane containing 5 through 20 carbon atoms per molecule. Presently preferred such alkanes for use in producing a 2,6,-AMN product are n-octane, isooctane, and n-nonane (presently most preferred). A similar method is also presently believed to be useful for obtaining 2,6,7-ADMN in relatively high purity and in relatively high yield.

Any convenient acetylmethylnaphthalene isomer mixture may be used as a starting composition for the present recrystallization process. A present preference is to employ either the starting isomer mixture produced from the hereinabove described acetylation followed conveniently by a separation procedure, such as hereinabove indicated, or an isomer mixture as derived from another source, e.g., from a fractional distillation, or the like.

In one presently preferred mode of recovery of 2,6-AMN, a vacuum fractional distillation of a starting isomer mixture is carried out to remove almost all of the 2,8-AMN and preferably also some of the 2,7-AMN. Preferably, the recovered isomer mixture contains at least about 87 weight percent of 2,6-AMN. Since the 2,7-AMN has a boiling point that is very close to that of the 2,6-AMN, it is not always economical or practically possible to upgrade all of the produced 2,6-AMN to a 95 percent purity level by distillation alone. In view of this circumstance, a side stream from the reboiler of the fractional distillation column can be continuously separated during the distillation recovery procedure. Such a stream typically contains about 87 weight percent 2,6-AMN and about 13 weight percent 2,7-AMN on a 100 weight percent total stream basis. This stream can then be collected and purified by the recrystallization process as presently taught herein.

In another procedure, such as when a fractional distillation is either not practical, or not economically feasible, the entire initially produced isomer mixture can be purified by the aforedescribed recrystallization process to achieve the desired 95 weight percent pure 2,6-AMN recovered product.

This recrystallization procedure involves preliminary dissolution of the isomer mixture in an alkane, such as n-nonane (presently most preferred). Preferably, the isomer mixture is one which has been produced by a preliminary fractional distillation of a starting isomer mixture, as above described, and the residue is used for the present recrystallization procedure. A present preference is to employ a weight ratio of isomer mixture to alkane solvent in range from about 0.1 to about 2, although larger and smaller such ratios may be used, if desired. At the time of dissolution, the temperature of the isomer mixture and of the alkane is preferably in the range of about 25° C. to about 90° C. (80° F. to 200° F.), although higher and lower such temperatures may be employed, if desired.

After such dissolution, the product solution is chilled, preferably to a temperature in the range of about 0° C. to about 25° C. (35° F. to 80° F.), although higher and lower temperatures can be employed, if desired. The chilling results in the formation of crystals of purified 2,6-AMN which can be separated as desired, usually by filtration or centrifuging.

For example, for an isomer mixture feed containing 87.6 weight percent 2,6-AMN with the remainder being mainly 2,7-AMN, a product of the desired minimal approximately 95 weight percent purity in a 2,6-AMN yield over 95 weight percent (based on 2,6-AMN) can be obtained by a crystallization technique in n-nonane at about 15.6° C. (60° F.) and at a 2:1 solvent to isomer mixture weight ratio. Solids/liquid separation of crystallized solids can be accomplished by filtration, centrifuging, or the like, as desired.

For another example, an isomer mixture freshly obtained directly from acetylation followed by a separation procedure, such as above indicated, and which contains a relatively lower concentration 2,6-AMN can be purified to the desired 95 weight percent purity 2,6-AMN in a multi-step crystallization procedure. Thus, such a starting isomer mixture is dissolved, preferably in n-nonane, at about 38° C. (100° F.) followed by cooling, crystal formation and separation. The separated product is then preferably redissolved with some solvent at about the same temperature, preferably in n-nonane at about 38° C. (100° F.), followed again by cooling, crystal formation and separation. Using a two-step procedure, an overall yield of about 85 weight percent is obtainable (based on starting 2,6-AMN present in the starting isomer mixture) of at least about 95 weight percent purity 2,6-AMN.

A comparison of the alkanes n-octane, n-nonane, and n-decane as solvents for recrystallization of 2,6-AMN in accord with the present invention is provided below. In general, experience indicates that n-nonane is better at separating 2,7-AMN without losing 2,6-AMN than any other known solvent; hence, the present preference for n-nonane as the solvent for recrystallization.

Isooctane is also a fairly effective medium for purifying 2,6-AMN as exemplified below. However, purities in excess of about 95 weight percent for 2,6-AMN appear to be difficult to obtain using isooctane as solvent because its relative selectivity towards 2,7-AMN in comparison to, or in relation to, 2,6-AMN is not as good as that of n-octane or n-nonane.

An evaluation of various possible alternative solvents as possible media for recrystallization of 2,6-AMN was carried out as exemplified below.

The following examples are offered to specifically illustrate this invention. These examples are not to be construed as limiting the scope thereof, however.

In each of the following examples, unless otherwise indicated, the reaction flask wherein the condensing of acetyl chloride with 2-methylnaphthalene compound occurred was initially cooled in an ice bath (0° C.) to compensate for the exothermicity of reaction. After combination of all reactants, the flask was allowed to warm to room temperature for the remainder of the reaction.

EXAMPLE 1

Synthesis of 2,6-AMN by Acetylation of 2-MN with Nitrobenzene using Addition of Acetyl Chloride to 2-MN and AlCl₃ (Bouveault Method)

To a stirred 250 ml round bottom flask was added 10 ml of nitrobenzene, and the flask was cooled in an ice bath. To this was added 1.96 g of $AlCl_3$, then 1.81 g of 2-methylnaphthalene (2-MN) and then 20 ml of additional nitrobenzene. To the chilled homogeneous dark-brown mixture was added 1.10 g of acetyl chloride by use of a syringe pump over a period of three minutes, resulting in formation of a reddish-brown solution. After allowing the solution to warm up to room temperature with subsequent stirring for a total reaction time of 24 hours, the product mixture was poured into a beaker containing 100 ml of concentrated hydrochloric acid and 25 ml of crushed ice. The resulting solution was transferred to a separator funnel and to this was added 125 ml of ether. After vigorous shaking, the aqueous layer was allowed to settle and was discarded. In like manner, the ether layer was then washed with 125 ml portions of 3 M aqueous hydrochloric acid, water, 10 percent aqueous sodium bicarbonate, and then water. The organic layer was dried over magnesium sulfate, filtered, and most of the ether was stripped away by use of a rotary evaporator. Analysis by gas chromatography (G.C.) revealed a 75 percent conversion of 2-MN and a 71 percent selectivity to 2,6-AMN. The two major by-products were 2,7-AMN and 1,6-AMN. A separate experiment carried out to higher conversion revealed: 85 percent conversion and 77 percent selectivity.

EXAMPLE 2

Synthesis of 2,6-AMN by Acetylation of 2-MN with Nitrobenzene using Addition of Acetyl Chloride to 2-MN and AlCl₃ (Bouveault Method)

In a procedure similar to that of Example 1, above, the reaction was carried out and worked up in the same manner except that a total of 15 ml of nitrobenzene was used instead of 30 ml.

Analysis: 86% Conversion of 2-MN, 72% Selectivity of 2,6-AMN.

EXAMPLE 3

Synthesis of 2,6-AMN by Acetylation of 2-MN with Nitrobenzene using Addition of 2-MN to Acetyl Chloride and AlCl₃ (Perrier Method)

A procedure similar to that of Example 1 was carried out again, except that a 10 ml solution of the 2-MN was added to a solution of the acetyl chloride and $AlCl_3$.

Analysis of product revealed a 78 weight percent conversion of 2-MN and a 70 percent selectivity to 2,6-AMN.

EXAMPLE 4

Synthesis of 2,6-AMN by Acetylation of 2-MN with Nitrobenzene using Addition of AlCl₃ to 2-MN + Acetyl Chloride (Elbs Method)

A procedure similar to that of Example 1 was carried out again, except a total of 2.05 g of solid $AlCl_3$ was added over a period of 30 min to a solution of the acetyl chloride and 2-MN in 30 ml of nitrobenzene.

Analysis revealed an 83 percent conversion of 2-MN and an 81 percent selectivity to 2,6-AMN.

EXAMPLE 5

Separation of AlCl₃ from a Product Liquid Mixture Containing Aromatic Ketone Aluminum Chloride Reaction Product To 2500 gm of a product solution prepared according to Example 2, above, was added 2500 gm of methanol. To this was added 5000 gm of water and the 2-phase mixture was stirred vigorously for 30 minutes. After allowing the mixture to settle cleanly into two layers, the top aqueous phase was removed and discarded. To the organic layer was added another 5000 gm portion of hot (95° C. or 203° F.) water containing 10 percent $NaHCO_3$. After stirring, settling, and isolation of the layers, the organic phase was analyzed by X-ray fluorescence and found to contain <10 ppm of Al.

EXAMPLE 6

Synthesis of 2,6-AMN by Acetylation of 2-MN with Nitrobenzene using Addition of 2-MN to Acetyl Chloride and AlCl₃ (Perrier Method)

To a stirred round bottom flask was added 1.70 g (12.7 mmol) of $AlCl_3$ and then 5 ml (5.98 g, 48.6 mmol) of nitrobenzene. To this mixture was added 25 ml of benzene solvent which resulted in the formation of a clear yellow solution. The flask and its contents were chilled in an ice bath. Then 1.81 g (12.7 mmol) of 2-methylnaphthalene was added all at once, and, after it was completely dissolved, 1.00 g (12.7 mmol) of acetyl chloride was added dropwise over a period of several minutes which resulted in the formation of a deep yellow solution containing a small amount of dispersed solids. The solution was allowed to warm to room temperature. After one hour of stirring, 1 ml of this slurry was quenched in 2 ml of conc. $NH_4OH$, shaken, and extracted with about 4 ml of ether. The ether solution was evaporated to about one-half of its original volume and analyzed by gas-liquid chromatography. After 19 hours of stirring, another 1 ml of the reaction mixture was similarly quenched and analyzed. The conversion and selectivity are shown in Table I, below, and were estimated based on a G.C. area percent analytical method. In the procedure of this example, and, in general, for the procedure employed in all examples herein, conversion and selectivity was essentially unchanged between 1 hour and about 17-24 hours of reaction time.

EXAMPLE 7

Synthesis of 2,6-AMN by Acetylation of 2-MN with Nitrobenzene using Addition of AlCl₃ (Elbs Method)

To a stirred round bottom flask was added 1.81 g (12.7 mmol) of 2-methylnaphthalene, 2.35 g of nitrobenzene (1.91 mmol), 30 ml of ethylene dichloride solvent, and 1.10 g (14.0 mmol) of acetyl chloride which resulted in a clear, colorless solution. The flask and its contents were chilled in an ice bath. To this was added 1.87 g (14.0 mmol) of aluminum chloride in small increments over a period of 5 minutes which resulted in a dark mustard colored liquid reaction mixture. The mixture was allowed to warm to room temperature. This was sampled, quenched, and analyzed at 1 hour and again at 17 hours of reaction time. Results are shown in Table I below.

EXAMPLE 8

Synthesis of 2,6-AMN by Acetylation of 2-MN with Nitrobenzene using Addition of Acetyl Chloride and AlCl₃ to 2-MN (Solvated Complex Addition or retro-Perrier Method)

The results are shown in Table I below.

In all examples shown in Table I, the reaction temperature is initially 0° C. (32° F.) and is terminally 20° C. (68° F.). Reaction products shown in each example are based on one hour of reaction time, but results appear to be the same after a reaction time of 17 to 24 hours.

TABLE I

| | | Nitrobenzene as Complexing Agent in Various Solvents | | | | |
|---|---|---|---|---|---|---|
| Ex. No. | Add. Meth. | Eq. Ratio NB$^{(4)}$/2-MN | Solvent | Solv. Ratio,$^{(10)}$ ml/g of 2-MN | % Conv.$^{(8)}$ | % Select. to 2,6-AMN$^{(9)}$ |
| 6 | B$^{(1)}$ | 3.82 | PH$^{(5)}$ | 13.81 | 61.8 | 57.9 |
| 7 | E$^{(2)}$ | 1.50 | EC$^{(7)}$ | 16.57 | 84.0 | 46.5 |
| 8 | S$^{(3)}$ | 3.82 | PH | 5.52 | 81.3 | 60.4 |
| 9 | B | 1.50 | MC$^{(6)}$ | 14.92 | 64.1 | 52.6 |
| 10 | B | 2.48 | MC | 13.81 | 82.8 | 54.9 |
| 11 | S | 3.82 | EC | 5.52 | 81.3 | 62.4 |
| 12 | E | 2.41 | MC | 13.81 | 72.8 | 57.0 |
| 13 | S | 1.00 | MC | 16.57 | 82.4 | 50.9 |
| 14 | B | 0 | PH | 16.57 | 84.6 | 17.7 |
| 15 | B | 22.89 | NB$^{(4)}$ | 16.57 | 79.3 | 71.5 |
| 16 | B | 0 | MC | 16.57 | 83.8 | 8.68 |

Table I Footnotes:
$^{(1)}$"B" designates Bouveault Method
$^{(2)}$"E" designates Ebbs Method
$^{(3)}$"S" designates SCAM (or retro-Perrier Method)
$^{(4)}$"NB" designates nitrobenzene
$^{(5)}$"PH" designates benzene
$^{(6)}$"MC" designates methylene dichloride
$^{(7)}$"EC" designates 1,2-dichloroethane
$^{(8)}$"% Conv." designates weight percent 2-MN consumed
$^{(9)}$"% Select. to 2,6-AMN" designates selectivity to 2,6-AMN from 2-MN
$^{(10)}$Ratio stated does not include nitrobenzene except in Example 15

To a stirred round bottom flask was added 1.81 g (12.7 mmol) of 2-methylnaphthalene and 5 ml of benzene solvent which resulted in a clear colorless solution. The flask and its contents were chilled in an ice bath. To an addition funnel was added a solution consisting of 1.70 g (12.7 mmol) of aluminum chloride in 5 ml (5.98 g, 48.6 mmol) of nitrobenzene, and then 1.01 g (12.9 mmol) of acetyl chloride. The resulting brown solution was added dropwise over a period of several minutes to the reaction flask which resulted in the formation of a light brown solution containing a small amount of dispersed solids. The solution was allowed to warm to room temperature. The reaction mixture was sampled, quenched, and analyzed at 1 hour and again at 24 hours of elapsed reaction time. Results are shown in Table I below.

EXAMPLES 9–16

Synthesis of 2,6-AMN by Acetylation of 2-MN with Nitrobenzene using Bouveault, Elbs, and retro-Perrier Methods Using the respective procedures of Examples 6, 7 and 8, a series of reactions of 2-MN and acetyl chloride in solution and in the presence of AlCl₃ and nitrobenzene as complexing agent were carried out to show the behavior of nitrobenzene as a complexing agent in various solvents.

EXAMPLES 17–22

Effect of Increasing Steric Hindrance on Nitrobenzenoid Compounds used as Complexing Agents in Aluminum Trichloride Catalyzed Synthesis of 2,6-AMN from 2-MN and Acetylchloride 30.3 mmol of nitrobenzene (3.88 g), o-nitrotoluene (4.16 g) and nitromesitylene (5.0 g) were each separately dissolved in individual 25 ml portions of ethylene dichloride (because nitromesitylene is a solid at ambient conditions).

An equivalent ratio of 2.48 moles of nitrobenzenoid compound (nitrobenzene, o-nitrotoluene, and nitromesitylene, as the case may be for each example) per mole of 2-MN was used in a run using each such nitrobenzenoid compound. The solvent ratio was 13.8 ml ethylene dichloride per gram of 2-MN. A Bouveault addition procedure (acetyl chloride added to 2-MN reactant) was used for each run (as described in Example 1 above. The initial reaction temperature was 0° C. (32° F.) and the final reaction temperature was 20° C. (68° F.). Reaction times for each run were one hour and also 17–24 hours.

Weight percent conversion (based on 2-MN) measured after 24 hours was similar for all three runs and ranged from about 83 to 90 weight percent. Results are shown in Table II below. o-Nitrotoluene and nitromesitylene are seen to be superior to nitrobenzene as complexing agents in this reaction.

TABLE II

| | | Various Nitroaromatic Complexing Agents | | | | |
|---|---|---|---|---|---|---|
| Ex. No. | C.A.$^{(5)}$ | Eq. Ratio NBZ$^{(1)}$/2-MN | Solv. | Solv. Ratio,$^{(2)}$ ml/g of 2-MN | % Conv.$^{(3)}$ | % Select. to 2,6-AMN$^{(4)}$ |
| 17 | NB$^{(6)}$ | 2.48 | EC$^{(9)}$ | 13.81 | 82.8 | 54.9 |
| 18 | NT$^{(7)}$ | 2.48 | EC | 13.81 | 90.3 | 65.1 |
| 19 | NM$^{(8)}$ | 2.48 | EC | 13.81 | 86.2 | 62.5 |
| 20 | NB | 22.9 | NB | 16.57 | 79.3 | 71.5 |
| 21 | NT | 20.0 | NT | 16.57 | 80.0 | 75.9 |

TABLE II-continued

| | | Various Nitroaromatic Complexing Agents | | | |
|---|---|---|---|---|---|
| Ex. No. | C.A.[5] | Eq. Ratio NBZ[1]/2-MN | Solv. | Solv. Ratio,[2] ml/g of 2-MN | % Conv.[3] | % Select. to 2,6-AMN[4] |
| 22 | NT | 5.00 | NT | 4.15 | 85.1 | 66.3 |

Table II Footnotes:
[1]Heading designates equivalent weight of particular nitrobenzenoid compound (NBZ) per equivalent of 2-MN
[2]Solvent ratio expressed as milliliters of solvent per gram of 2-MN
[3]"% Conv." designates weight percent 2-MN consumed
[4]"% Select. to 2,6-AMN" designates % selectivity to 2,6-AMN from 2-MN consumed
[5]"C.A." designates complexing agent
[6]"NB" designates nitrobenzene
[7]"NT" designates o-nitrotoluene
[8]"NM" designates nitromesitylene
[9]"EC" designates 1,2-dichloroethane

EXAMPLES 23-28

Comparison of Regiospecific Activity for Beta Position of Naphthalene for (a) Solvent and (b) Solvent Plus Complexing Agent Nitrobenzene was evaluated in several solvents (benzene, methylene dichloride, and 1,2-dichloroethane) under comparable conditions as a complexing agent for the acetylation of 2-MN with acetyl chloride and AlCl₃.

The procedure for each run utilized either the Bouveault addition method (acetyl chloride added to other reactants), or the Ebbs addition method (AlCl₃ added to other reactants) as shown in Table III below. The reaction temperature was 0° C. (32° F.) initially, and 20° C. (68° F.) terminally. Reaction time was one hour. All runs used the same reaction stoichiometry of 1.0/1.0/1.0 of 2-MN/acetyl chloride/AlCl₃.

Results are shown in Table III below.

EXAMPLES 29-33

Synergistic Complexing Action of Nitrobenzene and Hexamethylbenzene in Synthesis of 2,6-AMN from 2-MN and Acetyl Chloride Using the retro-Perrier addition procedure (see Example 8) wherein acetyl chloride and AlCl₃ are added to other reactants and methylene dichloride is employed as the solvent, nitrobenzene and hexamethylbenzene are evaluated individually and in combination as complexing agents for the making of 2,6-AMN from 2-MN and acetyl chloride using AlCl₃ catalyst.

The reaction temperature initially was 0° C. (32° F.) and terminally 20° C. (68° F.). The reaction time was one hour. The solvent ratio was 16.6 ml methylene dichloride per gram of 2-MN.

The weight percent conversion of 2-MN and the percent selectivity to various acetylmethylnaphthalene isomers are measured and shown in Table IV below.

TABLE III

| | | Evaluation of Solvent Effect | | | | |
|---|---|---|---|---|---|---|
| Ex. No. | Solvent System Type & Amt. | Addition Method | % Conv.[7] | % Select. to 2,6-AMN | 2,8-AMN | 2,6-AMN |
| 23 | PH[2] (30 ml) | B[5] | 85 | 18 | 45 | 27 |
| 24 | PH[2] (25 ml) + NB[1] (3.8 eq) | E[6] | 60 | 52 | 34 | 10 |
| 25 | CH₂Cl₂[3] (25 ml) | B | 84 | 9 | 26 | 62 |
| 26 | CH₂Cl₂[3] (25 ml) + NB[1] (2.4 eq) | E | 73 | 57 | 20 | 11 |
| 27 | (CH₂)₂Cl₂[4] (25 ml) | B | 86 | 21 | 27 | 42 |
| 28 | (CH₂)₂Cl₂[4] (25 ml) + NB[1] (2.5 eq) | B | 78 | 55 | 27 | 8 |

Table III Footnotes
[1]"NB" designates nitrobenzene
[2]"PH" designates benzene
[3]"CH₂Cl₂" designates methylene dichloride
[4]"(CH₂)₂Cl₂" designates 1,2-dichloroethane
[5]"B" designates Bouveault addition method
[6]"E" designates Elbs addition method
[7]"% Conv." designates weight 2-MN consumed

TABLE IV

| | | Evaluation of Synergistic Action of Nitrobenzene and Hexamethylbenzene in Methylene Dichloride as Complexing Agents | | | | | | |
|---|---|---|---|---|---|---|---|---|
| Ex. No. | Complexing Agent (type and eq. wt.) | % Conv.[4] | % Selectivity to Acetylmethylnaphthalene Isomers | | | | | |
| | | | 2,1 | 2,8 | 2,7 | 2,6 | Σ | Other |
| 29 | 1 eq. NB[1] | 8.24 | 7.87 | 26.90 | 7.40 | 50.91 | 93.08 | 6.92 |
| | | | | −13.6 ↓ | | +14.8 ↓ | | |
| 30 | 1 eq. HMB[2] | 90.6 | 8.93 | 13.26 | 6.81 | 65.74 | 94.74 | 5.26 |
| | | | | −5.2 ↓ | | +4.9 ↓ | | |
| 31 | 0.5 eq. HMB[2] 0.5 eq. NB[1] | 86.3 | 3.70 | 13.11 | 7.17 | 70.62 | 94.60 | 5.40 |
| 32 | 15.6 eq. NB[1] | 85.5 | 3.82 | 11.74 | 8.33 | 72.07 | 95.96 | 4.04 |

TABLE IV-continued

Evaluation of Synergistic Action of Nitrobenzene and
Hexamethylbenzene in Methylene Dichloride as Complexing Agents

| Ex. No. | Complexing Agent (type and eq. wt.) | % Conv.[4] | % Selectivity to Acetylmethylnaphthalene Isomers | | | | | |
|---|---|---|---|---|---|---|---|---|
| | | | 2,1 | 2,8 | 2,7 | 2,6 | Σ | Other |
| 33 | (11.3 solv. ratio)[5] CH$_2$Cl$_2$ 16.6 solv. ratio[5] | 83.8 | 61.86 | 25.65 | | 8.68 | 96.19 | 3.81 |

Table IV Footnotes
[1]"NB" designates nitrobenzene
[2]"HMB" designates hexamethylbenzene
[3]"CH$_2$Cl$_2$" designates methylene dichloride
[4]"% Conv." designates weight percent 2-MN consumed
[5]"solv. ratio" designates milliliters of solvent per gram of 2-MN

EXAMPLES 34–44

Recrystallization of 2,6-AMN from n-Nonane Solution of Isomer Mixture

Each one of a series of acetylmethylnaphthalene isomer mixtures was dissolved in n-nonane at 38° C. (100° F.). Each such mixture was comprised mainly 2,6-AMN with the remainder being 2,7-AMN (2-acetyl-7-methylnaphthalene). The 2,6-AMN content of each such mixture is shown in Table V below. Also shown in Table V for each such solution is the weight ratio of solvent to total isomer mixture and the temperature of the dissolution.

Thereafter, each such solution was chilled to about 15.5 to about 21° C. (60° to 69° F.). The crystals formed were removed by filtration.

In the cases of Examples 34–37, 43 and 44, the product crystals were not washed, but in the case of Examples 38–42, the product crystals were washed with additional n-nonane using a weight ratio and n-nonane temperature as shown in Table V.

The weight percent of 2,6-AMN in the recovered product (purity), and the weight percent of 2,6-AMN recovered relative to the total weight percent of 2,6-AMN in the starting isomer mixture (yield) are shown in Table V.

As Example 44 shows, for a feed containing 87.6 percent 2,6-AMN, with the remainder being 2,7-AMN, a desired 95 percent purity, together with a high yield of over 95 percent (based on 2,6-AMN in the feed) was achieved using a crystallization in n-nonane at 60° F. and 2:1 solvent ratio. Alternatively, as indicated by Examples 43 and 44, an isomer mixture resulting from the reaction of 2-MN with acetyl chloride as taught herein and containing 75 percent 2,6-AMN after being stripped of nitrobenzene complexing agent, solvent, and excess 2-MN, was purified to 95 percent 2,6-AMN in a two step crystallization having an overall yield of 85 percent.

TABLE V 2,6-AMN Recrystallization from n-Nonane

| Ex. No. | 2,6-AMN Content of Starting Mixture Wt.-% (1) | Solvent to Mixture Weight Ratio and Temp. | Wash | Wt.-% of 2,6-AMN in Product | Yield of 2,6-AMN Recovered % |
|---|---|---|---|---|---|
| 34 | 73.7 | 1:1 70° F. | X | 77.9 | 96.7 |
| 35 | 73.7 | 2:1 70° F. | X | 85.2 | 72.7 |
| 36 | 73.7 | 3:1 70° F. | X | 92.6 | 69.6 |
| 37 | 73.7 | 4:1 60° F. | X | 94.1 | 70.8 |
| 38 | 73.7 | 4:1 60° F. | 3:1 40° F. | 98.9 | 71.3 |
| 39 | 87.6 | 4:1 70° F. | 3:1 40° F. | 99.4 | 73.3 |
| 40 | 87.6 | 4:1 60° F. | 3:1 40° F. | 99.2 | 74.5 |
| 41 | 87.6 | 3:1 60° F. | 3:1 40° F. | 98.7 | 80.9 |
| 42 | 87.6 | 2:1 70° F. | 3:1 40° F. | 94.5 | 90.7 |
| 43 | 73.7 | 2:1 60° F. | X | 85.2 | 87.5 |
| 44 | 87.6 | 2:1 60° F. | X | 94.4 | 96.8 |

Table V Footnote:
(1) Balance of starting isomer mixture is comprised of 2,7-AMN.

EXAMPLE 45

Recrystallization of 2,6-AMN from n-Nonane Solution of Isomer Mixture

A crude isomer mixture weighing 33.71 grams and containing 59.4 weight 2,6-AMN, 12.8 weight percent nitrobenzene and 27.8 weight percent of other materials which were believed to be mainly other isomers of acetylmethylnaphthalene was used for the present evaluation.

This isomer mixture was dissolved in 150 ml (105.45 g) of n-octane at about 21° C. (70° F.) and cooled to about 7° C. (45° F.) where crystals were formed and separated by filtration.

After two washes of the recovered crystals with n-octane at about 7° C. (45° F.), the first wash using 15 ml of n-octane, and the second wash using 10 ml of n-octane, 14.34 grams of recrystallized solids were recovered.

The mother liquor was subjected to evaporation using a rotary evaporator and was thus concentrated to a residual weight of 19.37 grams.

The results are summarized in Table VI below:

TABLE VI

Recrystallization of 2,6-AMN in n-Octane

| Wt.-% 2,6-AMN in starting mixture | Ratio of Solvent to starting isomer mixture | Wash Weight ratio of solvent to crystallized product | Wt.-% of 2,6-AMN in Product | Yield of 2,6-AMN, % |
|---|---|---|---|---|
| 59.4% (12.8% NB) | 4.5:1 @ 70° F. | 1) 0.14:1 2) 0.49:1 both @ 45° F. | 86.6% | 62.1% |

The results indicate that n-octane can be used as a solvent for recrystallization of 2,6-AMN.

EXAMPLE 46

Comparison of n-Octane, n-Nonane, and n-Decane as Solvents

A crude isomer mixture was preliminarily found by analysis to have the following composition:

| Isomer Mixture Component | Wt.-% (Total Wt. Basis) |
|---|---|
| 2,6-AMN | 87.60 |
| 2,7-AMN | 9.60 |
| Other Isomers | 2.80 |
| Total | 100.00 |

Four gram samples of this isomer composition were dissolved in each of n-octane, n-nonane and n-decane at a 3:1 weight ratio of solvent to isomer mixture at 38° C. (100° F.). The solution was then cooled to about 15.6° C. (60° F.) here a crystallized product formed and was separated. In each case, this product was washed with 12 grams of the same solvent at 4.4° C. (39° F.). The yields of respective isomers recovered in the respective products after analysis thereof was found to be as shown in the following Table VII:

TABLE VII

Comparison of n-Octane, n-Nonane and n-Decane as Solvents

| Solvent | AMN Isomer in Recovered Product, Wt.-% | | | Yield of 2,6-AMN Recovered, % |
|---|---|---|---|---|
| | 2,6 | 2,7 | 2,8 | |
| n-octane | 97.5 | 2.1 | .2 | 78.3 |
| n-nonane | 98.2 | 1.8 | 0 | 85.6 |
| n-decane | 96.4 | 3.6 | 0 | 72.4 |

While all these solvents were suitable, based upon the foregoing results n-nonane gave the highest yield and highest purity.

EXAMPLE 47

Comparison of n-Octane and n-Nonane

A mixed AMN isomer mixture having the following composition was used:

| Isomer Mixture Component | Wt.-% (Total Wt. Basis) |
|---|---|
| 2,6-AMN | 73.7% |
| Other Isomers | 26.3% |

Four gram samples of the isomer mixtures were dissolved in each of n-octane and n-nonane at a 4:1 weight ratio of solvent to isomer mixture at 38° C. (100° F.). The solution is then cooled to about 15.5° C. (60° F.) where a crystallized product formed and was separated. The product was not washed. The yields of respective isomers recovered in the respective products after analysis thereof was found to be as shown in the following Table VIII:

TABLE VIII

Comparison of n-Octane and n-Nonane as Solvent

| Solvent | AMN Isomer in Recovered Product, Wt.-% | | | Yield of 2,6-AMN Recovered, % |
|---|---|---|---|---|
| | 2,6 | 2,7 | 2,8 | |
| n-octane | 92.7 | 3.2 | 2.2 | 63.7 |
| n-nonane | 94.1 | 2.7 | 1.7 | 70.8 |

As the data shown in Tables VII and VIII demonstrates, n-nonane was found to be the better recrystallization solvent under the conditions employed.

EXAMPLE 48

Recrystallization with Isooctane

A series of acetylmethylnaphthalene isomer mixtures, each one containing a different amount of 2,6-AMN, were recrystallized with isooctane:

Each sample was dissolved in isooctane at about 38° C. (100° F.) and then cooled to the temperature shown in Table IX below. Crystallized solids were separated therefrom. Thereafter, each so produced solid particulate product was washed with an additional quantity of the same solvent. The washed product was analyzed. Results are shown in Table IX below:

TABLE IX

Solubility of Mixed Isomers in Isooctane

| Starting 2,6-AMN % (1) | Dissolution Solvent to Isomer Mixture Weight Ratio | Cryst. Temp. | Solvent to Crystal Weight Ratio | Wash Temp. | Wash Wt.-% of 2,6-AMN in Cryst. Product | Yield of 2,6-AMN Recov'd, % |
|---|---|---|---|---|---|---|
| 73.7 | 3:1 | 70° F. | 1:1 | 70° F. | 90.0 | 65.9 |
| 73.7 | 2:1 | 70° F. | 1:1 | 70° F. | 86.9 | 81.9 |
| 73.7 | 3:1 | 70° F. | 1:1 | 70° F. | 87.4 | 76.6 |
| 73.7 | 4:1 | 60° F. | 1:1 | 70° F. | 85.6 | 79.3 |
| 73.7 | 3:1 | 50° F. | 1:1 | 70° F. | 84.0 | 81.7 |
| 83.0 | 4:1 | 70° F. | 1:1 | 70° F. | 93.4 | 88.0 |
| 83.0 | 3:1 | 70° F. | 1:1 | 70° F. | 92.8 | 89.6 |

Table IX Footnote:
(1) Indicates 2,6-AMN content in starting isomer mixture, wt.-%.

EXAMPLE 49

Comparative Study of Solvents for Isomer Mixture

In place of alkane hydrocarbons, various other solvents were evaluated as media for possible use in recrystallizing 2,6-AMN from isomer mixtures.

Thus, various 2,6-AMN isomer mixtures derived from the acetylation process steps hereinabove described were dissolved in each of various solvents, all as shown in Table X below. The crystallized product recovered on cooling of each solution of dissolved isomer mixture is analyzed for purity and yield. Results are shown in Table X below. From Table X, it is seen that all of the solvents evaluated were inferior to alkanes for purposes of recrystallization of 2,6-AMN from acetylmethylnaphthalene isomer mixtures.

TABLE X

Comparative Study of Various Solvents for Isomer Mixture

| Solvent | Solvent Weight Ratio | Cryst. Temp | Starting Wt.-% 2,6-AMN | Wt.-% of 2,6-AMN in Product | Yield of 2,6-AMN Recov'd, % | Comments |
|---|---|---|---|---|---|---|
| 95% | 2:1 | 70° F. | 83.0 | 0 | 0 | |
| Acetic | 2:1 | 50° F. | 83.0 | 0 | 0 | |
| Acid | 2:1 | 40° F. | 83.0 | 0 | 0 | |
| | 2:1 | 18° F. | 83.0 | 0 | 0 | Froze |
| | 1:1 | 15° F. | 83.0 | 0 | 0 | Froze |
| | 0.5:1 | 15° F. | 83.0 | 0 | 0 | Froze |
| Cyclohexane | 4:1 | 60° F. | 83.0 | 87.0 | 46.2 | |
| Methanol | 2:1 | 52° F. | 73.7 | 92.8 | 49.2 | |
| | 1:1 | 50° F. | 73.7 | 87.6 | 52.6 | |
| N-Butanol | 1:1 | 65° F. | 73.7 | 82.7 | 66.4 | |
| Propanol | 2:1 | 60° F. | 73.7 | 77.4 | 83.7 | |
| | 0.5:1 | 70° F. | 73.1 | 73.9 | 82.9 | |
| Hexane | | | | (high) | (low) | |
| Isopar[(1)] | | | | (low) | (high) | |

Table X footnotes:
[(1)]"Isopar" is a trademark of the Humble Oil and Refining Co. for a brand of high-purity isoparaffinic solvent.

The foregoing specification is intended as illustrative and is not to be taken as limiting. Still other variations within the spirit and the scope of the invention are possible and will readily present themselves to those skilled in the art.

We claim:

1. A process for making a 2-acyl-6-methylnaphthalene compound which comprises the steps of:
   (A) combining
      a 2-methyl substituted naphthalene compound selected from the group consisting of 2-methylnaphthalene and 2,3-dimethylnaphthalene with
      an acylation complex constituted by a Friedel-Crafts catalyst, a $C_1$–$C_6$ hydrocarbyl acylating agent, at least one thermally stable nitrohydrocarbon complexing agent which is selected from the group consisting of nitrobenzene, an alkyl substituted nitrobenzene, a dinitrobenzene, an alkyl substituted dinitrobenzene, a nitronaphthalene, an alkyl substituted mononitronaphthalene, a dinitronaphthalene, an alkyl substituted dinitronaphthalene, a nitrobiphenyl, an alkyl substituted mononitrobiphenyl, a dinitrobiphenyl, an alkyl substituted dinitrobiphenyl, nitro alkenes, nitrosubstituted cycloolefins, nitro furans, nitro thiophenes, nitro pyrroles, nitrosubstituted metallocenes, and mixtures thereof, wherein said alkyl groups contain 1 through 4 carbon atoms per alkyl group, and an electron-rich complexing agent selected from the group consisting of peralkylated aromatic hydrocarbons, sterically hindered aliphatic compounds, peralkylated metallocenes, peralkylated heterocyclic ring compounds, and mixtures thereof, in an acylation inert organic solvent that is liquid at 0° C. so as to produce a reaction mixture containing an aromatic ketone/Friedel-Crafts catalyst reaction product; and
   (B) removing said catalyst from said reaction mixture to produce a 2-acyl-6-methylnaphthalene-rich acylmethylnaphthalene isomer mixture.

2. The process of claim 1 wherein said acylating agent is acetyl chloride.

3. A process for making a 2-acetyl-6-methylnaphthalene compound which comprises the steps of:
   (A) combining
      a 2-methyl substituted naphthalene compound selected from the group consisting of 2-methylnaphthalene and 2,3-dimethylnaphthalene with
      an acylation complex constituted by a Friedel-Crafts catalyst, acetyl chloride, at least one thermally stable nitrohydrocarbon complexing agent which is selected from the group consisting of nitrobenzene, an alkyl substituted nitrobenzene, a dinitrobenzene, an alkyl substituted dinitrobenzene, a nitronaphthalene, an alkyl substituted mononitronaphthalene, a dinitronaphthalene, an alkyl substituted dinitronaphthalene, a nitrobiphenyl, an alkyl substituted mononitrobiphenyl, a dinitrobiphenyl, an alkyl substituted dinitrobiphenyl, nitro alkenes, nitrosubstituted cycloolefins, nitro furans, nitro thiophenes, nitropyrroles, nitrosubstituted metallocenes, and mixtures thereof, wherein said alkyl groups contain 1 through 4 carbon atoms per alkyl group, and an electron-rich complexing agent selected from the group consisting of peralkylated aromatic hydrocarbons, sterically hindered aliphatic compounds, peralkylated metallocenes, peralkylated heterocyclic ring compounds, and mixtures thereof, in an inert organic solvent that is liquid at 0° C. so as to produce a reaction mixture containing an aromatic ketone/Friedel-Crafts catalyst reaction product;
   (B) combining said reaction mixture with a solubilizing agent for said Friedel-Crafts catalyst to produce a water-extractable catalyst complex, said solubilizing agent comprising an aliphatic monohydric alcohol containing up to about 12 carbon atoms per molecule, inclusive; and
   (C) removing said catalyst complex from said reaction mixture to produce a 2-acetyl-6-methylnaphthalene-rich acetylmethylnaphthalene isomer mixture.

4. The process of claim 1 wherein said Friedel-Crafts catalyst is aluminum chloride.

5. The process of claim 1 wherein said 2-methylnaphthalene compound is 2-methylnaphthalene and said isomer mixture is rich in 2-acetyl-6-methylnaphthalene.

6. The process of claim 1 wherein said 2-methylnaphthalene compound is 2,3-dimethylnaphthalene and said isomer mixture is rich in 2-acetyl-6,7-dimethylnaphthalene.

7. The process of claim 1 wherein all said alkyl substituents in said nitrohydrocarbon complexing agents are methyl.

8. The process of claim 1 wherein said nitrobenzenoid complexing agent is selected from the group consisting of nitrobenzene, o-nitrotoluene, and nitromesitylene.

9. The process of claim 8 wherein said complexing agent is nitrobenzene.

10. A regioselective process for making a 2-acetyl-6-methylnaphthalene compound which comprises the successive steps of
(A) combining
a 2-methylnaphthalene compound selected from the group consisting of 2-methylnaphthalene and 2,3-dimethylnaphthalene with
an acylation complex constituted by aluminum trichloride, acetyl chloride, at least one thermally stable nitrobenzenoid complexing agent which is selected from the group consisting of:
nitrobenzene;
an alkyl-substituted mononitrobenzene containing 1 through 4 carbon atoms per alkyl group;
a dinitrobenzene;
an alkyl-substituted dinitrobenzene containing 1 through 4 carbon atoms per alkyl group;
a nitronaphthalene;
an alkyl substituted mononitronaphthalene containing 1 through 4 carbon atoms per alkyl group;
a dinitronaphthalene;
an alkyl substitued dinitronaphthalene containing 1 through 4 carbon atoms per alkyl group;
a nitrobiphenyl;
an alkyl substituted mononitrobiphenyl containing 1 through 4 carbon atoms per alkyl group;
dinitrobiphenyl;
an alkyl substituted dinitrobiphenyl containing 1 through 4 carbon atoms per alkyl group; and mixtures thereof, with an electronrich complexing agent selected from the group consisting of peralkylated aromatic hydrocarbons, sterically hindered aliphatic compounds, peralkylated metallocenes, peralkylated heterocyclic ring compounds, and mixtures thereof, to produce a liquid reaction mixture, said 2-methylnaphthalene compound and said acylation complex each being preliminarily dissolved in an inert organic solvent that is a liquid at 0° C. and is a solvent to all reactants present, said complexing agent, and for said aluminum chloride, yet is substantially completely inert relative thereto; said solvent being selected from the group consisting of an aromatic hydrocarbon compound, a halohydrocarbon compound, and mixtures thereof; and thereafter
(B) separating from said liquid reaction mixture said aluminum chloride, residual said 2-methylnaphthalene compound, and said solvent to produce a product isomer mixture comprised of acetylmethylnaphthalene isomers.

11. The process of claim 10 wherein said 2-methylnaphthalene compound is 2-methylnaphthalene and said isomer mixture is rich in 2-acetyl-6-methylnaphthalene.

12. The process of claim 10 wherein said separating is carried out by the steps of:
(A) adding to said liquid reaction mixture a solubilizing agent comprising an aliphatic monohydric alcohol having up to about 12 carbon atoms per molecule, inclusive, which forms a soluble complex with aluminum trichloride which complex is water stable and water soluble;
(B) extracting said reaction mixture with water to remove said water soluble aluminum trichloride complex from said reaction mixture; and
(C) recovering said isomer mixture from said so extracted liquid reaction mixture.

13. The process of claim 12 wherein a 2-acetyl-6-methylnaphthalene compound is isolated from said isomer mixture.

14. The process of claim 12 wherein said aliphatic monohydric alcohol is methanol and the weight ratio of said reaction mixture to said methanol is in the range of about 20:1 to about 1:20, respectively.

15. The process of claim 10 wherein said nitrobenzenoid complexing agent is nitrobenzene.

16. The process of claim 13 wherein said isolation of said 2-acetyl-6-methylnaphthalene compound is carried out by dissolving said isomer mixture in an alkane hydrocarbon compound containing 5 to 20 carbon atoms, inclusive, then cooling such resulting solution to precipitate said 2-acetyl-6-methylnaphthalene, and then recovering said precipitate.

17. The process of claim 16 wherein said alkane comprises n-nonane.

18. The process of claim 13 wherein said isolation of said 2-acetyl-6-methylnaphthalene is carried out by the steps of first fractionally distilling said isomer mixture to recover a high purity 2-acetyl-6-methylnaphthalene compound, then dissolving the residue from such distillation in an alkane hydrocarbon selected from the group consisting of n-octane, isooctane, and n-nonane, then cooling the resulting solution to crystallize said 2-acetyl-6-methylnaphthalene compound, and then separating said so crystallized 2-acetyl-6-methylnaphthalene compound.

19. The process of claim 1 wherein the acylation complex is constituted by said nitrobenzenoid complexing agent and said electron-rich, carbon-based complexing agent in an equivalent ratio in the range of about 10:1 to about 1:10, respectively.

20. The process of claim 1 wherein said nitrobenzenoid complexing agent is selected from the group consisting of nitrobenzene, nitromesitylene and nitrotoluene, wherein said electron-rich, carbon-based complexing agent is hexamethylbenzene and wherein said $C_1$–$C_6$ hydrocarbyl acylating agent is acetyl chloride.

21. The process of claim 20 wherein said inert solvent is methylene dichloride.

22. The process of claim 20 wherein said inert solvent is 1,2-dichloroethane.

23. A process for making a 2-acyl-6-methylnaphthalene compound which comprises the steps of:
(A) combining
a 2-methyl substituted naphthalene compound selected from the group consisting of 2-methylnaphthalene and 2,3-dimethylnaphthalene with,
an acylation complex constituted by a Friedel-Crafts catalyst, a $C_1$–$C_6$ hydrocarbyl acylating agent, and at least one thermally stable nitrobenzenoid complexing agent selected from the group consisting of nitrotoluene and nitromesitylene, in an inert organic solvent that is liquid at 0° C. so as to produce a reaction mixture containing an aromatic ketone/Friedel-Crafts catalyst reaction product; and (B) removing said catalyst from said reaction mixture to produce a 2-acyl-6-methylnaphthalene-rich acylmethylnaphthalene isomer mixture.

24. The process of claim 23 wherein said Friedel-Crafts catalyst is aluminum trichloride, said 2-methyl substituted naphthalene compound is 2-methyl naphthalene, and said solvent is selected from the group consisting of benzene, methylene dichloride and 1,2-dichloroethane.

25. The process of claim 8 wherein said electron-rich complexing agent is hexamethylbenzene.

26. The process of claim 10 wherein said nitrobenzenoid complexing agent is selected from the group consisting of nitrobenzene, o-nitrotoluene and nitromesitylene, and wherein said electron-rich complexing agent is hexamethylbenzene.

27. A regioselective process for making a 2-acetyl-6-methylnaphthalene compound which comprises the successive steps of (A) combining
  a 2-methylnaphthalene compound selected from the group consisting of 2-methylnaphthalene and 2,3-dimethylnaphthalene with
  an acylation complex constituted by aluminum trichloride, acetyl chloride, and at least one thermally stable nitrobenzenoid complexing agent which is selected from the group consisting of:
  nitrobenzene;
  an alkyl-substituted mononitrobenzene containing 1 through 4 carbon atoms per alkyl group;
  a dinitrobenzene;
  an alkyl-substituted dinitronaphthalene containing 1 through 4 carbon atoms per alkyl group;
  a nitronaphthalene;
  an alkyl substituted mononitronaphthalene containing 1 through 4 carbon atoms per alkyl group;
  a dinitronaphthalene;
  an alkyl substituted dinitronaphthalene containing 1 through 4 carbon atoms per alkyl group;
  a nitrobiphenyl;
  an alkyl substituted mononitrobiphenyl containing 1 through 4 carbon atoms per alkyl group;
  a dinitrobiphenyl;
  an alkyl substituted dinitrobiphenyl containing 1 through 4 carbon atoms per alkyl group;
  and mixtures thereof, to produce a liquid reaction mixture, said 2-methylnaphthalene compound and said acylation complex each being preliminarily dissolved in an inert organic solvent that is a liquid at 0° C. and is a solvent to all reactants present, said complexing agent, and for said aluminum chloride, yet is substantially completely inert relative thereto; said solvent being selected from the group consisting of an aromatic hydrocarbon compound, a halohydrocarbon compound, and mixtures thereof; and wherein a solution of said acetyl chloride, said aluminum trichloride, and said nitrobenzenoid complexing agent in said solvent is separately prepared and then added to a solution of said 2-methylnaphthalene in said solvent to achieve said combining, and thereafter (B) separating from said liquid reaction mixture said aluminum chloride, residual said 2-methylnaphthalene compound, and said solvent to produce a product isomer mixture comprised of acetylmethylnaphthalene isomers.

28. The process of claim 27 wherein said nitrobenzenoid complexing agent is nitrobenzene.

29. The process of claim 28 wherein said nitrobenzene is present in an amount of about 0.5 to about 5 moles of nitrobenzene per mole of 2-methylnaphthalene compound.

30. The process of claim 24 wherein said hydrocarbon is nonane.

* * * * *